US006767903B1

(12) United States Patent
Cleve et al.

(10) Patent No.: US 6,767,903 B1
(45) Date of Patent: Jul. 27, 2004

(54) NEW 7α, 17α-BIS-ALKYLATED TESTOSTERONE DERIVATIVES AND THEIR USE IN LONG-TERM THERAPY OF ANDROGEN-DEPENDENT DISEASES

(75) Inventors: Arwed Cleve, Berlin (DE); Gerhard Sauer, Berlin (DE); Christoph Huwe, Berlin (DE); Karsten Parczyk, Berlin (DE); Jens Hoffmann, Muhlenpeck (DE); Martin Schneider, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 09/869,000
(22) PCT Filed: Dec. 23, 1999
(86) PCT No.: PCT/EP99/10355
§ 371 (c)(1),
(2), (4) Date: Aug. 23, 2001
(87) PCT Pub. No.: WO00/39148
PCT Pub. Date: Jul. 6, 2000

Related U.S. Application Data
(60) Provisional application No. 60/124,048, filed on Mar. 12, 1999.

(30) Foreign Application Priority Data

Dec. 23, 1998 (DE) .......................................... 198 60 719

(51) Int. Cl.[7] .......................... A61K 31/59; A61K 31/57; C07J 1/00; C07J 5/00
(52) U.S. Cl. ...................... 514/182; 514/169; 514/177; 552/623; 552/625; 552/505
(58) Field of Search ................................. 552/623, 625, 552/505, 590, 596; 514/177, 182, 169, 172, 178, 170, 171

(56) References Cited

U.S. PATENT DOCUMENTS 3,341,557 A 9/1967 Babcock et al.

FOREIGN PATENT DOCUMENTS

| WO | WO 9100732 | 1/1991 |
|---|---|---|
| WO | WO 9313122 | 7/1993 |

OTHER PUBLICATIONS

Solo et al: "7.alpha.–Alkyltestosterone derivatives: synthesis and activity as androgens and as aromatase inhibitors" Steroids, US, Elsevier Science Publishers, New York, NY, Bd. 40, Nr. Dec. 6, 1982 Seiten 603–614–614, XP002111323 ISSN: 0039–128 X.

C. Luderschmidt et al: "Relative Binding Affinity at Mer-tribolone Androgenic Binding Sites of Various Antiandrogenic Agents" Arzneimittel Forschung. Drug Research., Bd. 37, Nr. 10, Oct. 1987, Seiten 1262–1265, XP002134934 Editio Cantor Aulendorf., DE ISSN: 0004–4172.

J. R. Brooks et al: "Topical anti–androgenicity of a new 4–azasteroid in the hamster" Steroids: Structure, Function, and Regulation., Bd. 56, Nr. 8, Aug. 1991, Seiten 428–433, XP002134933 Elsevier Science Publishers, New York, NY., US ISSN: 0039–128X.

Chemical Abstracts, vol. 101, No. 11, Sep. 10, 1984 Columbus, Ohio, US; abstract No. 86527m DE Larminat, Marie Anne et al: "Synthesis and evaluation of immobilized androgens for affinity chromatography in the purification of nuclear androgen receptor" XP002134935 & Prostate (N.Y.) (1984), 5(2), 123–40.

*Primary Examiner*—Sabiha Qazi
(74) *Attorney, Agent, or Firm*—Millen White Zelano & Branigan, P.C.

(57) ABSTRACT

The invention relates to new 7α, 17α, 17β-substituted testosterone derivatives of general formula (I) and their use as pure antiandrogens for the long-term therapy of androgen-dependent diseases, notably for the long-term antiandrogen therapy of prostate carcinoma. In the general formula (I) A is an unbranched $C_6$–$C_{13}$-alkylene group; B is an oxygen atom, —S(O)$_p$— group, in which p is 0, 1 or 2, an iminocarbonyl group —C(O)N(Y)—, an imino group —N(Y)—, a carbonylimino group —N(Y)C(O)—, a sulfonylimino group —NN(Y)S(O)$_2$—, where Y is a hydrogen atom or a $C_1$–$C_8$-alkyl group, a sulfonyloxy group —OS(O)$_2$—, a dimethylsilyloxy group —O—Si(CH$_3$)$_2$— or a carbonylsulfanyl group —SC(O)— or a bond between A and C or, together with C, a bond between A and D; C is a bond between B and D or, together with B, a bond between A and D or an unbranched $C_1$–$C_6$-alkylene group, a phenylene group, a substituted phenylene group, a five-membered ring or six-membered ring heteroarylene group, a substituted five-membered ring or six-membered ring heteroarylene group or a five-membered ring or six-membered ring heteroarylene group fused with a phenyl ring; and D is a hydrogen atom, a $C_1$–$C_4$-alkyl group, a vinyl group, a $C_1$–$C_4$-alkoxy group, a $C_1$–$C_4$-alkoxycarbonyl group, a bis($C_1$–$C_4$-alkoxycarbonyl)methyl group, an acetyl ($C_1$–$C_4$-alkoxybonyl)methyl group, a cyan group, a carboxy group, an azide group, a hydroxy group, a halogen atom or a rest of the formula $C_nF_mH_o$, in which n is 1, 2, 3 or 4, m>1 and m+o=2n+1.

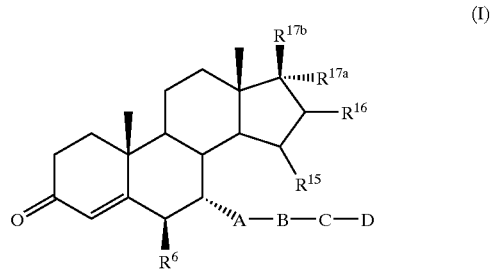

(I)

14 Claims, No Drawings

NEW 7α, 17α-BIS-ALKYLATED TESTOSTERONE DERIVATIVES AND THEIR USE IN LONG-TERM THERAPY OF ANDROGEN-DEPENDENT DISEASES

This application claims the benefit of the filing date of U.S. Provisional Application No. 60/124,048, filed Mar. 12, 1999.

This invention relates to new 7α, 17α, 17β-substituted testosterone derivatives of general formula I and their use as pure antiandrogens for long-term therapy for androgen-dependent diseases, especially for long-term antiandrogen therapy for prostate cancer.

Current therapies of androgen-dependent diseases are based on the reduction or as complete as possible elimination of androgen-induced effects. This can be done by blocking the domains of androgen receptor (AR), to which the androgens bind as ligands, or by reduction of the available amount of androgens themselves (ligand depletion). In prostate cancer treatment, "ligand depletions mean" a reduction of the serum testosterone level of testicular origin, which is to be achieved either with use of orchidectomy (removal of a testicle) or by hormone treatment with LRRH analogs or estrogens in high doses. This therapy for inhibiting androgen synthesis and/or reducing androgen concentration is effective only to a limited extent, however, since it has been noted in the meantime that even in the case of total absence of an androgen, non-blocked androgen receptors can be biologically active (ligand-independent AR activation).

As an alternative or as an amendment to "ligand depletion," the antiandrogen therapy is used, which is based on the antagonistic blocking of the androgen receptor by so-called "antiandrogens" (nonsteroidal or steroidal compounds). Known antiandrogens, which are already used in clinical practice for prostate cancer treatment, are CPA (Schering AG), flutamide (Schering Plough), Casodex (Zeneca) and Anandron$^{(R)}$ (Roussel).

Although 80% of patients first respond to the above-mentioned therapies, almost all of these patients suffer a relapse as early as after an average treatment period of 12–18 months. It has been shown that even the AR blocking by the currently available antiandrogens is inadequate, since the latter either have insufficient active strength and/or can even activate the androgen receptor, i.e. can act like androgens (partial agonism).

Compounds that can act as inhibitors of androgen synthesis and for as blockers of the androgen receptor are also described in WO91/00732. In this case, these are substituted steroids, which have at least one long side chain in one of positions 6α, 7α, 14α, 15α, 16α, 17α and 17β. Described as preferred compounds are EM 101, a testosterone that is substituted in 17β-position with hydroxy and in 7α-position with a long-chain alkylamide, and EM 150, a testosterone that is substituted in 17β-position with hydroxy and in 17α-position with a long-chain iodoalkine. These compounds also have the above-described drawbacks.

In summary, it has been determined that there is currently no satisfactory therapy for androgen-dependent diseases, such as, e.g., for prostate cancer, and in particular no long-term therapy is possible. The known antiandrogen compounds do not have the necessary active strength to ensure complete blocking of the androgen receptor activity or to have a partially agonistic action.

The object of this invention was therefore to provide potent antiandrogenic compounds that make possible a long-term therapy for androgen-dependent diseases. In particular, prostate cancer can be treated effectively with these compounds.

The object of this invention is achieved by new 7α-, 17α-, 17β-substituted testosterone derivatives of general formula I

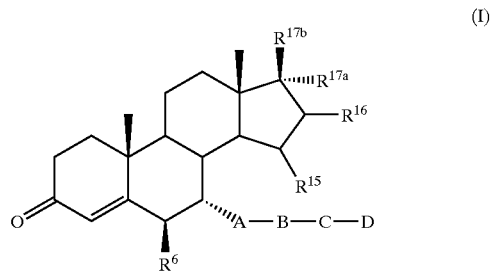

in which
$R^6$ represents a hydrogen atom, a hydroxy group, a $C_1$–$C_{10}$ alkoxy group, a $C_1$–$C_{10}$ alkanoyloxy group or a halogen atom, $R^{15}$ and $R^{16}$ each are a hydrogen atom or together form a bond, $R^{17a}$ represents a $C_1$–$C_4$ alkyl group, a $C_2$–$C_4$ alkinyl group, or a radical of Formula $C_nF_mH_o$, whereby n=1, 2, 3 or 4, m>1 and m+o=2n+1, $R^{17b}$ is a hydroxy group, a $C_1$–$C_{10}$ alkoxy group or a $C_1$–$C_{10}$ alkanoyloxy group, A is an unbranched $C_1$–$C_{13}$ alkylene group, B represents an oxygen n atom, a grouping —S(O)$_p$—, whereby p=0, 1 or 2, an iminocarbonyl group —C(O)N(Y)—, an imino group —N(Y)—, a carbonylimino group —N(Y)C(O)—, a sulfonylimino group —N(Y)S(O)$_2$—, whereby Y is a hydrogen atom or a $C_1$–$C_8$ alkyl group, a sulfonyloxy group —OS(O)$_2$—, a dimethylsilyloxy group —O—Si(CH$_3$)$_2$— or a carbonylsulfanyl group —SC(O)—, or B represents a bond between A and C or together with C forms a bond between A and D, C represents a bond between B and D, or together with B forms a bond between A and D or an unbranched, $C_1$–$C_6$ alkylene group, a phenylene group, a substituted phenylene group, a five-ring or six-ring heteroarylene group, a substituted five-ring or six-ring heteroarylene group or a five-ring or six-ring heteroarylene group that is condensed with a phenyl ring, and D represents a hydrogen atom, a $C_1$–$C_4$ alkyl group, a vinyl group, a $C_1$–$C_4$ alkoxy group, a $C_1$–$C_4$ alkoxycarbonyl group, a bis($C_1$–$C_4$ alkoxycarbonyl)methyl group, an acetyl($C_1$–$C_4$ alkoxycarbonyl)methyl group, a cyano group, a carboxy group, an azide group, a hydroxy group, a halogen atom or a radical of formula $C_nF_mH_o$, whereby n=1, 2, 3 or 4, m>1 and m+o=2n+1.

In a preferred embodiment of the invention, $R^{17a}$ in general formula I means the methyl or ethyl group or the trifluoromethyl or pentafluoroethyl group. Radical $R^{17b}$ preferably represents the hydroxy group, a $C_1$–$C_5$ alkoxy group or a $C_1$–$C_3$ alkanoyl group. Quite especially preferably, $R^{17b}$ means the hydroxy, methoxy, ethoxy or acetyloxy group. For radical $R^6$, a hydrogen atom, the hydroxy group or a halogen atom is preferred. In a quite especially preferred embodiment of the invention, the radical ABCD means 9-hydroxynonyl, 7-(acetylsulfanyl)heptyl or 7-(4-cyanobutoxy)heptyl.

For the purposes of this invention, the alkylene groups that are mentioned for grouping A are the heptane-1,7-diyl, the octane-1,8-diyl, the nonane-1,9-diyl, the decane-1,10-diyl, the undecane-1,11-diyl, the dodecane-1,12-diyl and the tridecane-1,13-diyl group. The equivalent applies for the alkylene groups that are defined as grouping C.

The alkyl groups that are mentioned for substituents Y and D stand both for the unbranched groups, i.e., the methyl, ethyl and propyl group, and the corresponding higher homologues, in so far as they are claimed, and for the branched representatives of the above-mentioned carbon atom numbers, e.g., the 1-methylethyl group, the 1-methylpropyl group, the 2-methylpropyl group, the 1,1-dimethylethyl group, etc. Moreover, alkyl groups are also to be defined as cyclic substituents, depending on the above-mentioned carbon atom number, e.g., the cyclopropyl, cyclopropylmethyl, cyclobutyl, cyclopentyl, methylcyclopentyl, cyclopentylmethyl and cyclohexyl radicals.

Alkoxy groups are radicals that are derived from the above-mentioned alkyl groups and extended by one oxygen atom, thus, e.g., the methoxy, ethoxy, propoxy, 1-methylethoxy, 1-methylpropoxy, 2-methylpropoxy and 1,1-dimethylethoxy radicals.

For the purposes of this invention, alkanoyloxy groups are defined as hydroxy groups that are esterified with branched and unbranched carboxylic acids of the above-mentioned numbers of carbon atoms, thus, e.g., the formyloxy, acetyloxy, 1-oxopropoxy, 1-oxobutoxy, and 2-methyl-1-oxopropoxy radical.

The arylene and heteroarylene groups that are indicated for grouping C are linked at a substitutable position with grouping B and substituted at another substitutable position with a radical D. Preferred heteroaromatic compounds are pyrrole, thiophene, imidazole, thiazole, oxazole, triazole, thiadiazole, indole, benzoxazole, benzothiazole, pyridine, and pyrimidine. In addition, the arylene or heteroarylene groups can be substituted with a methyl group or a halogen atom.

If a halogen atom is mentioned as a substituent in one of the radicals, a fluorine, chlorine, bromine or iodine atom is suitable for this purpose. Chlorine and fluorine are preferred.

For the purposes of the invention, the following compounds of general formula I are quite especially preferred:
1. 7α-(9-Chlorononyl)-17α-methyl-3-oxoandrost-4-en-17β-yl-acetate
2. 7α-(9-Chlorononyl)-17β-hydroxy-17α-methylandrost-4-en-3-one
3. 17β-Hydroxy-7α-(9-iodononyl)-17α-methylandrost-4-en-3-one
4. 17β-Hydroxy-7α-(9-hydroxynonyl)-17α-methylandrost-4-en-3-one
5. 7α-(10-Chlorodecyl)-17β-hydroxy-17α-methylandrost-4-en-3-one
6. 17β-Hydroxy-7α-(11-hydroxyundecyl)-17α-methylandrost-4-en-3-one
7. 7α-(11-Bromoundecyl)-17β-hydroxy-17α-methylandrost-4-en-3-one
8. 17β-Hydroxy-17α-methyl-7α-[7-(phenylsulfanyl)heptyl]-androst-4-en-3-one
9. 17β-Hydroxy-17α-methyl-7α-[9-[(4,4,5,5,5-pentafluoropentyl)sulfanyl]nonyl]androst-4-en-3-one
10. 17β-Hydroxy-17α-methyl-7α-[9-(phenylsulfanyl)nonyl]-androst-4-en-3-one
11. 7α-[9-[(5-Chloropentyl)sulfanyl]nonyl]-17β-hydroxy-17α-methylandrost-4-en-3-one
12. 17β-Hydroxy-7α-[9-[(5-hydroxypentyl)sulfanyl]nonyl]-17α-methylandrost-4-en-3-one
13. 7α-(9-Azidononyl)-17β-hydroxy-17α-methylandrost-4-en-3-one
14. 7α-[7-(Acetylsulfanyl)heptyl]-17β-hydroxy-17α-methylandrost-4-en-3-one
15. 17β-Hydroxy-17α-methyl-7α-[7-[(4,4,5,5,5-pentafluoropentyl)sulfanyl]heptyl]androst-4-en-3-one
16. N-[7-(17β-Hydroxy-17α-methyl-3-oxoandrost-4-en-7α-yl)heptyl]pentanamide
17. 17β-Hydroxy-17α-methyl-3-oxoandrost-4-en-7α-octane-nitrile
18. 5-[[7-(17β-Hydroxy-17α-methyl-3-oxoandrost-4-en-7α-yl)heptyl]oxy]pentanenitrile
19. 17β-Hydroxy-17α-methyl-7α-[9-[(4,4,5,5,5-pentafluoropentyl)sulfinyl]nonyl]androst-4-en-3-one
20. N-[9-(17β-Hydroxy-17α-methyl-3-oxoandrost-4-en-7α-yl)nonyl]methanesulfonamide
21. 7α-(9-Chlorononyl)-6β-hydroxy-17α-methyl-3-oxoandrost-4-en-17β-yl-acetate The production of the compounds according to the invention is carried out analogously to the synthesis methods that are described extensively in sterol and steroid literature. The following books form the basis for steroid synthesis: L. F. Fieser & M. Fieser: Steroids: Reinhold Publishing Corporation, NY 1959; Rood's Chemistry of Carbon Compounds (editor: S. Coffrey): Elsevier Publishing Company, 1971; and especially the "Dictionary of Steroids" (editors: R. A. Hill; D. N. Kirk; H. L. J. Makin and G. M. Murphy): Chapmann & Hall. The latter contains a detailed reference list of the original publications up to 1990.

The compounds of this invention can also be produced according to the following general synthesis diagrams and analogously to the production methods that are indicated in the examples. Preferably used as a starting compound is the 3-oxoandrosta-4,6-dien-17β-yl-acetate, whose production is described by Bowers et al. in J. Amer. Chem. Soc. 81, 5991 (1959).

For the case of the production of compounds with a perfluoroalkyl radical in 17α-position, the chain introduction in 7α-position is carried out according to Sakurai (cf. K. Nickisch, H. Laurent, Tetrahedron Lett. 29, 1533–1536 (1988)) with subsequent introduction of a carbonyl protective group in 3-position and subsequent introduction of the perfluoroalkyl radical in 17α-position according to the following diagram (cf. also Examples 1–43):

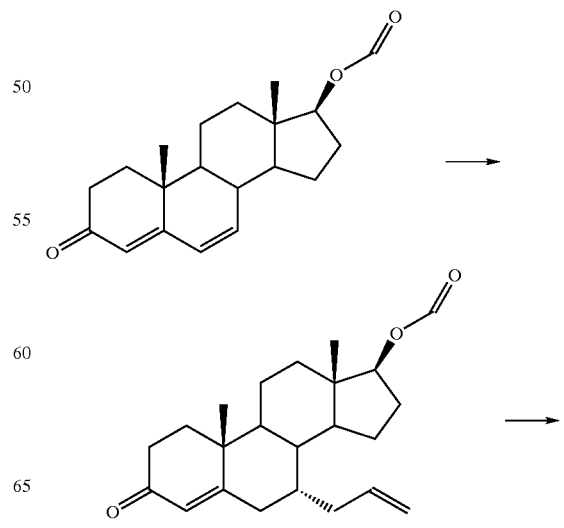

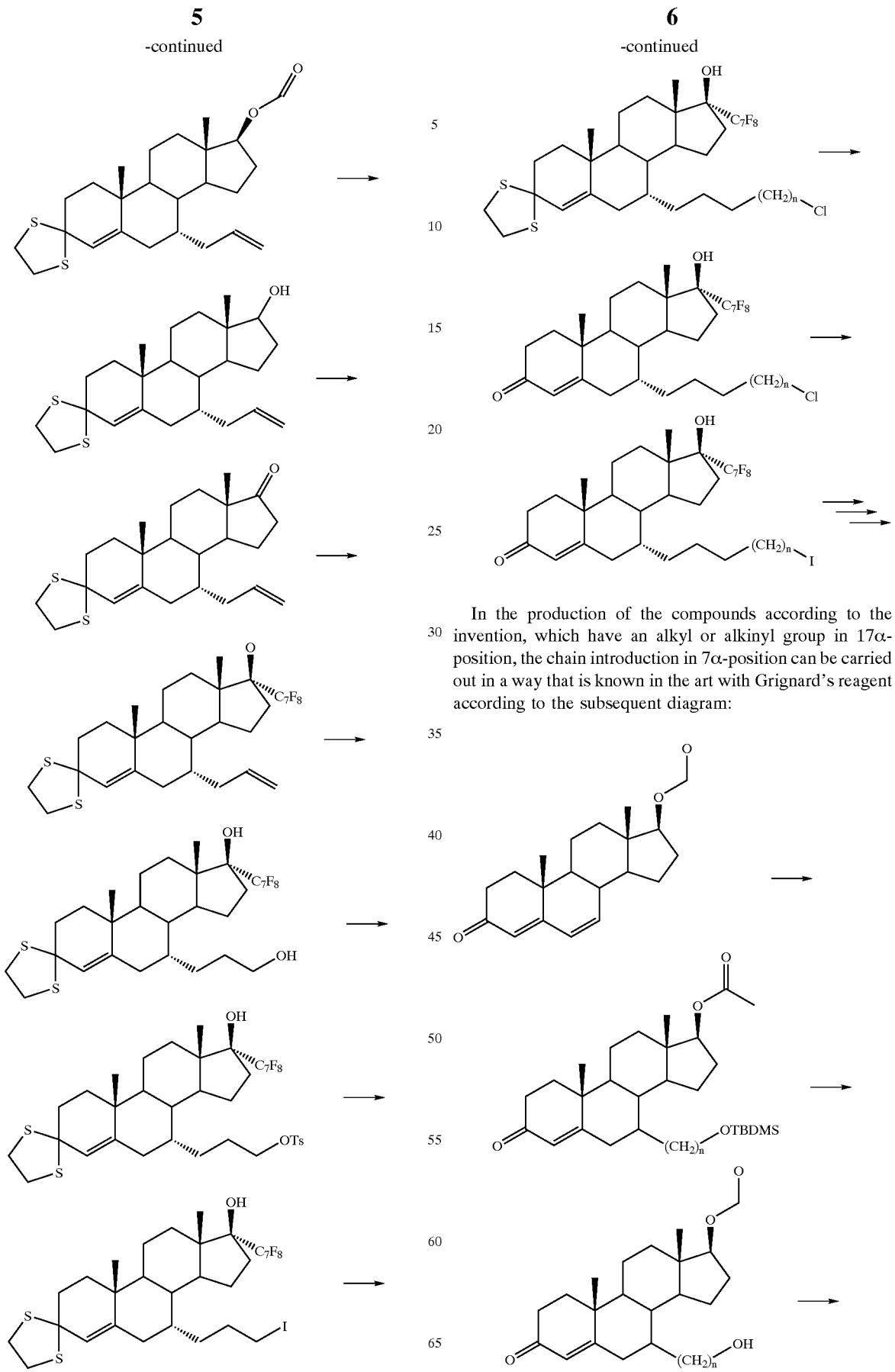
In the production of the compounds according to the invention, which have an alkyl or alkinyl group in 17α-position, the chain introduction in 7α-position can be carried out in a way that is known in the art with Grignard's reagent according to the subsequent diagram:

-continued

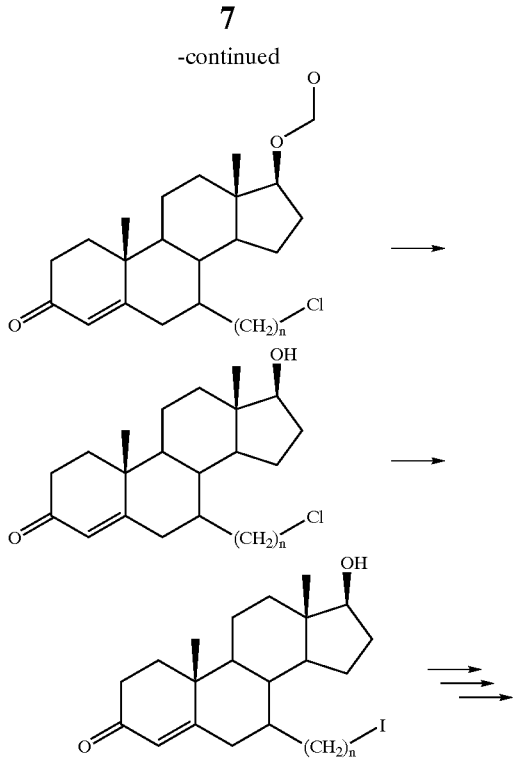

Additional derivatization of the alkylene iodide radical that is obtained in 7α-position is done according to commonly used organic synthesis methods and can be performed analogously to these examples.

It has now been found that the compounds of general formula I according to the invention act as pure antiandrogens and thus completely block the androgen receptor activity. The compounds completely inhibit the androgen-stimulated growth of the human prostate carcinoma cell line LNCaP. The compounds according to the invention are thus suitable for long-term antiandrogen therapy for androgen-dependent diseases, such as, for example, carcinoma of the prostate, common acne, hirsutism, early puberty, sexual deviations, androgenic alopecia, non-malignant prostatic hyperplasia or seborrhea.

The subject of the invention is therefore also the use of the compounds of general formula I according to the invention and the compounds, mentioned as preferred, for long-term antiandrogen therapy for androgen-dependent diseases, especially carcinoma of the prostate.

The compounds according to the invention are administered as pharmaceutical compositions, which contain therapeutically effective amounts of one or more compounds of general formula I and optionally galenical adjuvants and/or vehicles, which allow oral or parenteral administration of the agent. The preparations are administered in doses of 1–2000 mg, preferably 5–1000 mg per administration. The subjects of the invention are therefore also pharmaceutical agents, which contain at least one testosterone derivative of general formula I.

The invention is to be explained in more detail in the embodiments below.

EXAMPLE 1

7α-(8-Chlorooctyl)-17β-hydroxy-17α-(1,1,2,2,2-pentafluoroethyl)androst-4-en-3-one 1a) 3-Oxo-7α-(prop-2-enyl)androst-4-en-17β-yl-acetate 38.6 ml of titanium tetrachloride is slowly added in drops to a solution of 23.11 g of 3-oxoandrosta-4,6-dien-17β-yl-acetate, whose production is described in Bowers et al., J. Amer. Chem. Soc. 81, 5991 (1959), in 1200 ml of dichloromethane at −78° C. under nitrogen atmosphere. After ten minutes of stirring, 67 ml of trimethyl(prop-2-enyl)silane is added in drops at the same temperature. The reaction mixture is stirred for two hours at −78° C. and carefully mixed with water at this temperature. The organic phase is washed in succession with water, saturated aqueous sodium bicarbonate solution and saturated aqueous sodium chloride solution, dried on sodium sulfate, filtered and concentrated by evaporation in a vacuum. After column chromatography on silica gel with a mixture of hexane/ethyl acetate, 14.8 g of the title compound is obtained as a colorless foam.

$^1$H-NMR (CDCl$_3$): δ=5.72 s (1H, H-4); 5.64 m (1H, allyl); 5.02 dbr (J=10 Hz, 1H, allyl); 4.99 dbr (J=17 Hz, 1H, allyl); 4.61 ddbr (J=9 Hz+8 Hz, 1H, H-17); 2.05 s (3H, acetate); 1.20 s (3H, H-19); 0.85 s (3H, H-18).

1b) 3,3-[1,2-Ethanediylbis(thio)]-7α-(prop-2-enyl)androst-4-en-17β-yl-acetate 4.61 g of the compound that is produced under 1a) is dissolved in 50 ml of glacial acetic acid under nitrogen atmosphere and mixed with 1.04 ml of ethane-1,2-dithiol and with 1.18 g of 4-methylbenzenesulfonic acid monohydrate. The reaction mixture is stirred for four hours at room temperature, then: poured onto 900 ml of 2 molar aqueous sodium hydroxide solution and extracted with dichloromethane. The organic phase is washed in succession with water and saturated aqueous sodium chloride solution, dried on sodium sulfate, filtered and concentrated by evaporation in a vacuum. Column chromatography on silica gel with a mixture of hexane/ethyl acetate yields 4.99 g of the title compound as a colorless foam.

$^1$H-NMR (CDCl$_3$): δ=5.67 ddt (J=17 Hz+10 Hz+7 Hz, 1H, allyl); 5.45 s (1H, H-4); 5.05 dbr (J=17 Hz, 1H, allyl); 5.01 dbr (J=10 Hz, 1H, allyl); 4.58 ddbr (J=10 Hz+8 Hz, 1H, H-17); 3.43–3.28 m (3H, dithiolane); 3.28–3.15 m (1H, dithiolane); 2.05 s (3H, acetate); 1.04 s (3H, H-19); 0.81 s (3H, H-18).

1c) 3,3-[1,2-Ethanediylbis(thio)]-7α-(prop-2-enyl)androst-4-en-17β-ol 4.98 g of the compound that is described under 1b) is stirred with 1.69 g of potassium carbonate in 111 ml of methanol overnight at room temperature. The reaction mixture is largely concentrated by evaporation in a vacuum. The residue is taken up in water and extracted with ethyl acetate. The organic phase is washed in succession with water and saturated aqueous sodium chloride solution, dried on sodium sulfate, filtered and concentrated by evaporation in a vacuum. 4.48 g of 1c) is obtained, which is used as crude product in the next step.

$^1$H-NMR (CDCl$_3$): δ=5.67 ddt (J=17 Hz+10 Hz+7 Hz, 1H, allyl); 5.44 s (1H, H-4); 5.03 dbr (J=17 Hz, 1H, allyl); 5.01 dbr (J=10 Hz, 1H, allyl); 3.64 m (1H, H-17); 3.45 –3.29 m (3H, dithiolane); 3.29–3.15 m (1H, dithiolane); 1.05 s (3H, H-19); 0.77 s (3H, H-18).

1d) 3,3-[1,2-Ethanediyebis(thio)]-7α-(prop-2-enyl)androst-4-en-17-one 4.47 g of the compound that is produced under 1c) is dissolved in 110 ml of toluene and refluxed with 5.11 ml of cyclohexanone and with 1.01 g of aluminum triisopropylate for five hours in a water separator. For working-up, it is diluted with ethyl acetate, filtered on Celite(R), and rewashed with ethyl acetate. The filtrate is concentrated by evaporation in a Vacuum. Column chromatography of the residue on silica gel with a mixture of hexane/ethyl acetate yields 4.45 g of the title compound as a colorless foam.

$^1$H-NMR (CDCl$_3$): δ=5.69 ddt (J=17+Hz+10 Hz+7 Hz, 1H, allyl); 5.48 s (1H; H-4); 5.06 dbr (J=17 Hz, 1H, allyl);

5.04 dbr (J=10 Hz, 1H, allyl); 3.45–3.30 m (3H, dithiolane); 3.29–3.16 m (1H, dithiolane); 2.46 dd (J=18 Hz+9 Hz, 1H, H-16); 1.06 s (3H, H-19); 0.89 s) (3H, H-18).

1e) 3,3-[1,2-Ethanediylbis(thio)]-17α-(1,1,2,2,2-pentafluoroethyl)-7α-(prop-2-enyl)androst-4-en-17β-ol 22 g of 1,1,1,2,2-pentafluoro-2-iodoethane is condensed in 100 ml of toluene at room temperature under nitrogen and mixed at −78° C. with a solution of 4.44 g of the compound, produced under 1d), in 50 ml of toluene. After ten minutes, 51 ml of a 1.5 molar solution of methyllithium-lithium bromide complex in diethyl ether is slowly added in drops at the same temperature so that the internal temperature does not exceed −65° C. The reaction mixture is stirred in succession respectively for one hour at −78° C. and at 0° C., then poured onto saturated aqueous ammonium chloride solution and extracted with ethyl acetate. The organic phase is washed in succession with water and saturated aqueous sodium chloride solution, dried on sodium sulfate, filtered and concentrated by evaporation in a vacuum. After column chromatography on silica gel with a mixture of hexane/ethyl acetate, 5.67 g of the title compound is obtained as a colorless foam.

$^1$H-NMR (CDCl$_3$): δ=5.66 ddt (J=17 Hz+10 Hz+7 Hz, 1H, allyl); 5.45 s (1H, H-4); 5.05 dbr (J=17 Hz, 1H, allyl); 5.02 dbr (J=10 Hz, 1H, allyl); 3.43–3.29 m (3H, dithiolane); 3.29–3.16 m (1H, dithiolane); 2.39 m (1H, H-12); 1.04 s (3H, H-19); 0.97 s (3H, H-18).

1f) 3,3-[1,2-Ethanediylbis(thio)]-7α-(3-hydroxypropyl)-17α-(1,1,2,2,2-pentafluoroethyl)androst-4-en-17β-ol 1.1 ml of a 10 molar solution of borane-dimethyl sulfide complex in tetrahydrofuran is added in drops to a solution of 5.65 g of the compound, produced under 1e), in 110 ml of tetrahydrofuran at 0° C. under nitrogen atmosphere. After 90 minutes, 22 ml of 2 molar aqueous sodium hydroxide solution and 11 ml of 30% aqueous hydrogen peroxide solution are slowly added in drops at 0° C. The reaction mixture is stirred for one hour at −0° C., diluted with water and extracted with ethyl acetate. The organic phase is washed in succession with water and saturated aqueous sodium chloride solution, dried on sodium sulfate, filtered and concentrated by evaporation in a vacuum. Column chromatography on silica gel with a mixture of hexane/ethyl acetate yields 2.34 g of the title compound as a colorless foam.

$^1$H-NMR (CDCl$_3$): δ=5.48 s (1H, H-4); 3.64 m (2H, CH$_2$OH); 3.43–3.28 m (3H, dithiolane); 3.28–3.16 m (1H, dithiolane); 2.39 m (1H, H-12); 1.04 s (3H, H-19); 0.96 s (3H, H-18).

1g) 3-[3,3-[1,2-Ethanediylbis(thio)]17β-hydroxy-17α-(1,1,2,2,2-pentafluoroethyl)androst-4-en-7α-yl]propyl-(4-methylbenzenesulfonate)

2.3 g of the compound that is produced under 1f) is stirred with 3.26 g of 4-methylbenzenesulfonyl chloride and 6 ml of triethylazan in 85 ml of dichloromethane for four hours at room temperature under nitrogen atmosphere. The reaction mixture is poured into saturated aqueous sodium bicarbonate solution and extracted with ethyl acetate. The organic phase is washed in succession with water and saturated aqueous sodium chloride solution, dried on sodium sulfate, filtered and concentrated by evaporation in a vacuum. Column chromatography on silica gel with a mixture of hexane/ethyl acetate yields 1.8 g of the title compound as a colorless foam.

$^1$H-NMR (CDCl$_3$): δ=7,81 d (J=9 Hz, 2H, aryl); 7.37 d (J=9 Hz, 2H, aryl)=5.40 s (1H, H-4); 4.06 m (2H, CH$_2$OTs); 3.43–3.29 m (3H, dithiolane); 3.29–3.16 m (1H, dithiolane); 2.46 s (3H, tolyl); 2.36 m (1H, H-12); 1.02 s (3H H-19); 0.94 s (3H, H-18).

1h) 3,3-[1,2-Ethanediylbis(thio)]-7α-(3-iodopropyl)-17α-(1,1,2,2,2-pentafluoroethyl)androst-4-en-17β-ol 1.75 g of the compound that is produced under 1g) is refluxed overnight with 490 mg of sodium iodide in 25 ml of acetone. The reaction mixture is filtered, and the filtrate is concentrated by evaporation in a vacuum. Column chromatography on silica gel with a mixture of hexane/ethyl acetate yields 1.36 g of the title compound as a colorless foam.

$^1$H-NMR (CDCl$_3$): δ=5.48 s (1H, 9H-4); 3.44–3.29 m (3H, dithiolane); 3.29–3.15 m (1H, dithiolane); 3.18 t (J=7 Hz, 2H, CH$_2$I); 2.40 m (1H, H-12); 1.04 s (3H, H-19); 0.96 s (3H, H-18).

1i) 7α-(8-Chlorooctyl)-3,3-[1,2-ethanediylbis(thio)]-17α-(1,1,2,2,2-pentafluoroethyl)androst-4-en-17β-ol A solution of the Grignard compound 5-chloropentylmagnesium bromide is produced from 214 mg of magnesium chips in 2.2 ml of tetrahydrofuran by adding in drops a solution of 1.16 ml of 1-bromo-5-chloropentane in 6.6 ml of tetrahydrofuran at an internal temperature below 35° C. and with thirty more minutes of stirring. In another flask, a brown solution of dilithium tetrachlorocuprate is produced from 7.5 mg of lithium chloride and 11.8 mg of anhydrous copper(II) chloride in 0.88 ml of tetrahydrofuran by fifteen minutes of stirring at room temperature. 575 mg of the compound that is produced under 1h) and dissolved in 2 ml of tetrahydrofuran is added in drops to the above. At −10° C., the Grignard solution is added in drops to the steroid solution within one hour. During one more hour of stirring time, the reaction mixture reaches 0° C. It is then poured into saturated aqueous sodium bicarbonate solution and extracted with ethyl acetate. The organic phase is washed in succession with water and saturated aqueous sodium chloride solution, dried on sodium sulfate, filtered and concentrated by evaporation in a vacuum. After column chromatography on silica gel with a mixture of hexane/ethyl acetate, 342 mg of the title compound is obtained as a colorless oil.

$^1$H-NMR (CDCl$_3$): δ=5.46 s (1H, H-4); 3.54 t (J=7 Hz, 2H, CH$_2$Cl); 3.43–3.29 m (3H, dithiolane); 3.29–3.14 m (1H, dithiolane); 2.39 m (1H, H-12); 1.05 s (3H, H-19); 0.97 s (3H, H-18).

1j) 7α-(8-Chlorooctyl)-17β-hydroxy-17α-(1,1,2,2,2-pentafluoroethyl)androst-4-en-3-one 330 mg of the compound that is produced under 1i) is dissolved in 16 ml of glacial acetic acid, mixed with 2.43 g of glyoxylic acid and stirred for 15 minutes at room temperature. Then, 2 ml of 4 molar aqueous hydrochloric acid is added. After one hour of stirring at room temperature, the reaction mixture is added in drops to 500 ml of 2 molar aqueous sodium hydroxide solution and extracted with ethyl acetate. The organic phase is washed in succession with water and saturated aqueous sodium chloride solution, dried on sodium sulfate, filtered and concentrated by evaporation in a vacuum. Column chromatography on silica gel with a mixture of hexane/ethyl acetate yields 172 mg of the title compound as a colorless oil.

$^1$H-NMR (CDCl$_3$): δ=5.73 s (1H, H-4); 3.54 t (J=7 Hz, 2H, CH$_2$Cl); 1.21 s (3H, H-19); 1.00 s (3H, H-18).

EXAMPLE 2

17β-Hydroxy-7α-(8-iodooctyl)-17α-(1,1,2,2,2-pentafluoroethyl)androst-4-en-3-one 161 mg of the compound that is produced under 1j) is heated overnight to 80° C. with 87 mg of sodium iodide in 3 ml of 2-butanone. The reaction mixture is diluted with water and extracted with ethyl acetate. The organic phase is washed in succession with water and saturated aqueous sodium chloride solution, dried on sodium sulfate, filtered and concentrated by evaporation in a vacuum. Column chromatography on silica gel with a mixture of hexane/ethyl acetate yields 182 mg of the title compound as a colorless oil.

$^1$H-NMR (CDCl$_3$): δ=5.72 s (1H, H-4); 3.19 t (J=7 Hz, 2H, CH$_2$I); 1.21 s (3H, H-19); 1.00 s (3H, H-18).

EXAMPLE 3

17β-Hydroxy-3-oxo-17α-(1,1,2,2,2-pentafluoroethyl)androst-4-en-7α-nonane Nitrile 30 mg of the compound that is produced under 2) is stirred with 9 mg. of potassium cyanide in 1 ml of N,N-dimethylformamide for 16 hours at room temperature. The reaction mixture is diluted with water and extracted with ethyl acetate. The organic phase is washed with saturated aqueous sodium chloride solution, dried on sodium sulfate, filtered and concentrated by evaporation in a vacuum. Column chromatography on silica gel with a mixture of hexane/ethyl acetate yields 20 mg of the title compound as a colorless oil.

$^1$H-NMR (CDCl$_3$): δ=5.72 s (1H, H-4); 2.34 t (J=7 Hz, 2H, CH$_2$CN); 1.21 s (3H, H-19); 1.00 s (3H, H-18).

EXAMPLE 4

17β-Hydroxy-17α-(1,1,2,2,2-pentafluoroethyl)-7α-[8-(phenylsulfanyl)octyl]androst-4-en-3-one 80 mg of the compound that is produced under 2) is stirred with 22 mg of sodium phenyl thiolate in 1.5 ml of ethanol for 16 hours at 60° C. The reaction mixture is concentrated by evaporation in a vacuum and taken up in ethyl acetate. The organic phase is washed in succession with water and saturated aqueous sodium chloride solution, dried on sodium sulfate, filtered and concentrated by evaporation in a vacuum. Column chromatography on silica gel with a mixture of hexane/ethyl acetate yields 66 mg of the title compound as a colorless oil.

$^1$H-NMR (CDCl$_3$): δ=7.36–7.24 m (4H, aryl); 7.17 ddbr (J=8 Hz+8 Hz, 1H, aryl); 5.73 s (1H, H-4); 2.92 t (J=7 Hz, 2H, CH$_2$S); 1.21 s (3H, H-19); 1.00 s (3H, H-18).

EXAMPLE 5

17β-Hydroxy-17α-(1,1,2,2,2-pentafluoroethyl)-7α-[8-(phenylsulfinyl)octyl]androst-4-en-3-one 36 mg of the compound that is produced under 4) is dissolved in 0.34 ml of tetrahydrofuran, mixed with a solution of 55 mg of sodium periodate in 86 μl of water and 0.34 ml of methanol and stirred for 18 hours at room temperature. The reaction mixture is filtered, rewashed with ethylacetate and concentrated by evaporation in a vacuum. The residue is taken up in ethyl acetate and water. The organic phase is washed with saturated aqueous sodium chloride solution, dried on sodium sulfate, filtered and concentrated by evaporation in a vacuum. After column chromatography on silica gel with a mixture of hexane/ethyl acetate, 20 mg of the title compound is obtained as a colorless oil.

$^1$H-NMR (CDCl$_3$): δ=7.61 dbr (J=8 Hz, 2H, aryl); 7.57–7.45 m (3H, aryl); 5.72 s (1H, H-4); 2.79 t (J=7 Hz, 2H, CH$_2$SO); 1.21 s (3H, H-19); 1.00 s (3H, H-18).

EXAMPLE 6

7α-[8-[(2-Chlorophenyl)sulfanyl]octyl]-17β-hydroxy-17α-(1,1,2,2,2-pentafluoroethyl)androst-4-en-3-one 5.9 μl of 2-chlorobenzenethiol is added to a suspension of 2.1 mg of 60% sodium hydride as a dispersion in mineral oil in 1 ml of N,N-dimethylformamide. After one hour at room temperature, 30 mg of the compound that is produced under 2) and dissolved in 1 ml of N,N-dimethylformamide is added. The reaction mixture is stirred for 14 hours at room temperature, diluted with water and extracted with ethyl acetate. The organic phase is washed with saturated aqueous sodium chloride solution, dried on sodium sulfate, filtered and concentrated by evaporation in a vacuum. Column chromatography on silica gel with a mixture of hexane/ethyl acetate yields 17 mg of the title compound as a colorless oil.

$^1$H-NMR (CDCl$_3$): δ=7.36 dbr (J=8 Hz, 1H, aryl); 7.26 dbr (J=8 Hz, 1H, aryl); 7.22 ddbr (J=8 Hz+8 Hz, 1H, aryl); 7.09 ddbr (J=8 Hz+8 Hz, 1H, aryl); 5.73 s (1H, H-4); 2.93 t (J=7 Hz, 2H, CH$_2$S); 1.21 s (3H, H-19); 1.00 s (3H, H-18).

The following compounds were obtained analogously:

| Ex. | Product Reagent (Precursor/Process) | Form | Yield [%] | $^1$H-NMR δ |
|---|---|---|---|---|
| 7 | 17β-Hydroxy-17α-(1,1,2,2,2-pentafluoroethyl)-7α-[8-[(pyridin-2-yl)sulfanyl]octyl]androst-4-en-3-one Pyridine-2-thiol (2\6) | Foam | 41 | 8.42dbr(J=5Hz, 1H, pyridinyl); 7.47ddd(J=8Hz+8Hz+2Hz, 1H, pyridinyl); 7.17dbr(J=8Hz, 1H, pyridinyl); 6.96ddbr(J=8Hz+5Hz, 1H, pyridinyl); 5.72s(1H, H-4); 3.15t (J=7Hz, 2H, CH$_2$S); 1.20s (3H, H-19); 0.99s(3H, H-18) |
| 8 | 17β-Hydroxy-17α-(1,1,2,2,2-pentafluoroethyl)-7α-[8-[(pyrimidin-2-yl)sulfanyl]octyl]androst-4-en-3-one Pyrimidine-2-thiol (2\6) | Oil | 31 | 8.50d(J=5Hz, 2H, pyrimidinyl); 6.95t(J=5Hz, 1H, pyrimidinyl); 5.72s(1H, H-4); 3.14t (J=7Hz, 2H, CH$_2$S); 1.21s (3H, H-19); 1.00s(3H, H-18) |
| 9 | 7α-[8-[(Benzothiazol-2-yl)sulfanyl]-octyl]-17β-hydroxy-17α-(1,1,2,2,2-pentafluoroethyl)androst-4-en-3-one Benzothiazole-2-thiol (2\6) | Oil | 53 | 7.87dbr(J=8Hz, 1H, aryl); 7.76 dbr(J=8Hz, 1H, aryl); 7.41ddbr(J=8Hz+8Hz, 1H, aryl); 7.29ddbr(J=8Hz+8Hz, 1H, aryl); 5.73s(1H, H-4); 3.34t (J=7Hz, 2H, |

-continued

| Ex. | Product Reagent (Precursor/Process) | Form | Yield [%] | $^1$H-NMR δ |
|---|---|---|---|---|
| 10 | 7α-[8-[(6-Ethoxybenzothiazol-2-yl)sulfanyl]octyl]-17β-hydroxy-17α-(1,1,2,2,2-pentafluoroethyl)androst-4-en-3-one 6-Ethoxybenzothiazole-2-thiol (2\6) | Foam | 37 | 7.74d(J=9Hz, 1H, aryl); 7.22d(J=2Hz, 1H, aryl); 7.01 dd(J=9Hz+2Hz, 1H, aryl); 5.73s(1H, H-4); 4.08q(J=7Hz, 2H, OEt); 3.31t(J=7Hz, 2H, CH$_2$S); 1.44t(J=7Hz, 3H, OEt); 1.21s(3H, H-19); 1.00s(3H, H-18) |
| 11 | 17β-Hydroxy-17α-(1,1,2,2,2-pentafluoroethyl)-7α-[8-[(thiazol-2-yl)sulfanyl]octyl]androst-4-en-3-one Thiazole-2-thiol (2\6) | Oil | 51 | 7.66d(J=3Hz, 1H, thiazolyl); 7.20d(J=3Hz, 1H, thiazolyl); 5.73s(1H, H-4); 3.20t(J=7Hz, 2H, CH$_2$S); 1.21s(3H, H-19); 1.00s(3H, H-18) |
| 12 | 17β-Hydroxy-7α-[8-[(1-methyl-1H-imidazol-2-yl)sulfanyl]octyl]-17α-(1,1,2,2,2-pentafluoroethyl)androst-4-en-3-one 1-Methyl-1H-imidazole-2-thiol (2\6) | Oil | 57 | 7.05d(J=1Hz, 1H, imidazolyl); 6.92d(J=1Hz, 1H, imidazolyl); 5.72s(1H, H-4); 3.62s(3H, Me); 3.03t(J=7Hz, 2H, CH$_2$S); 1.21s(3H, H-19); 1.00s(3H, H-18) |
| 13 | 17β-Hydroxy-7α-[8-[(5-methyl-1,3,4-thiadiazol-2-yl)sulfanyl]octyl]-17α-(1,1,2,2,2-pentafluoroethyl)androst-4-en-3-one 5-Methyl-1,3,4-thiadiazole-2-thiol (2\6) | Oil | 60 | 5.72s(1H, H-4); 2.72s(3H, thiadiazolyl); 3.28t(J=7Hz, 2H, CH$_2$S); 1.21s(3H, H-19); 1.00s(3H, H-18) |
| 14 | 17β-Hydroxy-17α-(1,1,2,2,2-pentafluoroethyl)-7α-[8-[(thien-2-yl)sulfanyl]octyl]androst-4-en-3-one Thiophene-2-thiol (2\6) | Oil | 20 | 7.32dd(J=5Hz+1Hz, 1H, thienyl); 7.10dd(J=4Hz+1Hz, 1H, thienyl); 6.97dd(J=5Hz+4Hz, 1H, thienyl); 5.72s(1H, H-4); 2.79t(J=7Hz, 2H, CH$_2$S); 1.21s(3H, H-19); 1.00s(3H, H-18) |
| 15 | 2,2,3,3,4,4,4-Heptafluoro-N-[8-[17β-hydroxy-3-oxo-17α-(1,1,2,2,2-pentafluoroethyl)androst-4-en-7α-yl]octyl]butanamide 2,2,3,3,4,4,4-Heptafluorobutanamide (2\6) | Oil | 62 | 6.71sbr(1H, NH); 5.72s(1H, H-4); 3.38m(2H, CH$_2$N); 1.21s(3H, H-19); 1.00s(3H, H-18) |
| 16 | 17β-Hydroxy-7α-[8-[(4-methylphenyl)sulfonyl]octyl]-17α-(1,1,2,2,2-pentafluoroethyl)androst-4-en-3-one Sodium-4-methylbenzenesulfinate (2\4) | Oil | 64 | 7.79dbr(J=8Hz, 2H, aryl); 7.36 dbr(J=8Hz, 2H, aryl); 5.71s(1H, H-4); 3.06m(2H, CH$_2$SO$_2$); 2.45s(3H, tolyl); 1.21s(3H, H-19); 1.00s(3H, H-16) |
| 17 | 17β-Hydroxy-7α-[8-[(3-methylphenyl)sulfonyl]octyl]-17α-(1,1,2,2,2-pentafluoroethyl)androst-4-en-3-one Sodium-3-methylbenzenesulfinate, for production see B. Lindberg, Acta chem. Scand.17, 377–382 (1963) (2\4) | Oil | 22 | 7.62sbr(1H, aryl); 7.61m(1H, aryl); 7.46m(2H, aryl); 5.72s(1H, H-4); 3.06m(2H, CH$_2$SO$_2$); 2.46s(3H, tolyl); 1.21s(3H, H-19); 1.00s(3H, H-18) |
| 18a | 7α-(10-Bromodecyl)-3,3-[1,2-ethanediylbis(thio)]-17α-(1,1,2,2,2-pentafluoroethyl)androst-4-en-17β-ol 7-Bromoheptylmagnesium bromide (1h\1i) | Oil | 87 | 5.46s(1H, H-4); 3.45–3.29 m(3H, dithiolane); 3.29–3.15m (1H, dithiolane); 3.46t(J=7Hz, 2H, CH$_2$Br); 2.39m(1H, H-12) 1.04s(3H, H-19); 0.96s(3H, H-18) |
| 18b | 7α-(10-Bromodecyl)-17β-hydroxy-17α-(1,1,2,2,2-pentafluoroethyl)androst-4-en-3-one Glyoxylic acid/ glacial acetic acid (18a[1]j) | Oil | 22 | 5.73s(1H, H-4); 3.41t(J=7Hz, 2H, CH$_2$Br); 1.21s(3H, H-19); 1.00s(3H, H-18) |
| 19 | 17β-Hydroxy-17α-(1,1,2,2,2-pentafluoroethyl)-7α-[10-(phenylsulfanyl)decyl]androst-4-en-3-one Sodium phenylthiolate (18b\4) | Oil | 76 | 7.31dbr(J=8Hz, 2H, aryl); 7.27 ddbr(J=8Hz+8Hz, 2H, aryl:); 7.16 ddbr(J=8Hz+8Hz, 1H, aryl); 5.73s(1H, H-4); 2.91t(J=7Hz, 2H, CH$_2$S); 1.21s(3H, H-19); 0.99s(3H, H-18) |

-continued

| Ex. | Product Reagent (Precursor/Process) | Form | Yield [%] | ¹H-NMR δ |
|---|---|---|---|---|
| 20 | 17β-Hydroxy-17α-(1,1,2,2,2-pentafluoroethyl)-7α-[10-(phenylsulfinyl)decyl]androst-4-en-3-one<br>Sodium periodate (19\5) | Oil | 22 | 7.61dbr(J=8Hz, 2H, aryl); 7.57–7.48 m(3H, aryl); 5.73s (1H, H-4); 2.78t(J=7Hz, 2H, CH₂SO); 1.20s (3H, H-19); 1.00s(3H, H-18) |
| 21a | 3,3-[1,2-Ethanediylbis(thio)]-7α-(8-iodooctyl)-17α-(1,1,2,2,2-pentafluoroethyl)androst-4-en-17β-ol<br>Sodium iodide (1i\2) | Oil | 83 | 5.46s(1H, H-4); 3.43–3.29 m(3H, dithiolane); 3.29–3.14m (1H, dithiolane); 3.18t(J=7Hz, 2H, CH₂I); 2.39m (1H, H-12); 1.05s(3H, H-19); 0.97s (3H, H-18) |
| 21b | 7α-(13-Clortridecyl)-3,3-[1,2-ethanediylbis(thio)]-17α-(1,1,2,2,2-pentafluoroethyl)androst-4-en-17β-ol<br>5-Chloropentyl-magnesium bromide (21a\1i) | Oil | 43 | 5.46s(1H, H-4); 3.54t (J=7Hz, 2H, CH₂Cl); 3.43–3.29 m(3H, dithiolane); 3.29–3.14m (1H, dithiolane); 2.39m(1H, H-12); 1.05s (3H, H-19); 0.97s(3H, H-18) |
| 21c | 7α-(13-Chloro-tridecyl)-17β-hydroxy-17α-(1,1,2,2,2-pentafluoroethyl)androst-4-en-3-one<br>Glyoxylic acid/glacial acetic acid (21b\1j) | Oil | 72 | 5.73s(1H, H-4); 3.54t (J=7Hz, 2H, CH₂Cl); 1.21s (3H, H-19); 1.00s(3H, H-18) |
| 22 | 17β-Hydroxy-7α-(13-iodotridecyl)-17α-(1,1,2,2,2-pentafluoroethyl)androst-4-en-3-one<br>Sodium iodide (21c\2) | Oil | 86 | 5.72s(1H, H-4); 3.19t (J=7Hz, 2H, CH₂I); 1.21s (3H, H-19); 1.00s(3H, H-18) |
| 23 | 17β-Hydroxy-3-oxo-17α-(1,1,2,2,2-pentafluoroethyl)androst-4-ene-7α-tetradecane nitrile<br>Potassium cyanide (22\3) | Oil | 82 | 5.73s(1H, H-4); 2.34t (J=7Hz, 2H, CH₂CN); 1.21s (3H, H-19); 1.00s(3H, H-18) |
| 24 | 17β-Hydroxy-17α-(1,1,2,2,2-pentafluoroethyl)-7α-[13-(phenylsulfanyl)tridecyl]androst-4-eu-3-one<br>Sodium phenyl thiolate (22\4) | Oil | 87 | 7.36–7.22m (4H, aryl); 7.15ddbr(J=8Hz+8 Hz, 1H, aryl); 5.73s (1H, H-4); 2.91t(J=7Hz, 2H, CH₂S) 1.21s(3H, H-19); 1.00s (3H, H-18) |
| 25 | 17β-Hydroxy-17α-(1,1,2,2,2-pentafluoroethyl)-7α-[13-[(3-methyl-phenyl)sulfanyl]-tridecyl]androst-4-en-3-one<br>3-Methylbenzenethiol (22\6) | Oil | 47 | 7.18ddbr(J=8Hz+8Hz, 1H, aryl); 7.14sbr(1H, aryl); 7.12 dbr(J=8Hz, 1H, aryl); 6.98dbr(J=8Hz, 1H, aryl); 5.74s (1H, H-4); 2.91t(J=7Hz, 2H, CH₂S); 2.32s (1H, tolyl); 1.21s(3H, H-19); 1.00s (3H, H-18) |
| 26 | 17β-Hydroxy-17α-(1,1,2,2,2-pentafluoroethyl)-7α-[13-[(pyridin-2-yl)sulfanyl]tridecyl]androst-4-en-3-one<br>Pyridine-2-thiol (22\6) | Oil | 44 | 8.42dbr(J=5Hz, 1H, pyridinyl); 7.47ddd(J=8Hz+8Hz+2Hz, 1H, pyridinyl); 7.17dbr(J=8Hz, 1H, pyridinyl); 6.97ddbr(J=8Hz+5Hz, 1H, pyridinyl); 5.73s(1H, H-4); 3.15t (J=7Hz, 2H, CH₂S); 1.21s (3H, H-19); 0.99s(3H, H-18) |
| 27 | 17β-Hydroxy-17α-(1,1,2,2,2-pentafluoroethyl)-7α-[13-(pyrimidin-2-yl)sulfanyl]tridecyl]androst-4-en-3-one<br>Pyrimidine-2-thiol (22\6) | Oil | 31 | 8.50d(J=5Hz, 2H, pyrimidinyl); 6.94t(J=5Hz, 1H, pyrimidinyl); 5.72s(1H, H-4); 3.13t (J=7Hz, 2H, CH₂S); 1.21s (3H, H-19); 1.00s(3H, H-18) |
| 28 | 17β-Hydroxy-7α-[13-[(1-methyl-1H-imidazol-2-yl)sulfanyl]tridecyl]-17α-(1,1,2,2,2-pentafluoroethyl)androst-4-en-3-one<br>1-Methyl-1H-imidazole-2-thiol (22\6) | Oil | 27 | 7.06sbr(1H, imidazolidi-nyl); 6.92 sbr(1H, imidazolidi-nyl); 5.73s (1H, H-4); 3.62s(3H, NCH₃); 3.04t (J=7Hz, 2H, CH₂S); 1.21s(3H, H-19); 1.00s (3H, H-18) |
| 29 | 7α-[13-[(Benzothiazol-2-yl)sulfanyl]tridecyl]-17β-hydroxy-17α-(1,1,2,2,2-pentafluoroethyl)androst-4-en-3-one<br>Benzothiazole-2-thiol (22\6) | Oil | 35 | 7.87dbr(J=8Hz, 1H, aryl); 7.76 dbr(J=8Hz, 1H, aryl); 7.41ddbr(J=8Hz+8Hz, 1H, aryl); 7.31ddbr(J=8Hz+8Hz, 1H, aryl); |

-continued

| Ex. | Product Reagent (Precursor/Process) | Form | Yield [%] | ¹H-NMR δ |
|---|---|---|---|---|
| 30 | 7α-[13-[(6-Ethoxybenzothiazol-2-yl)sulfanyl]tridecyl]-17β-hydroxy-17α-(1,1,2,2,2-pentafluoroethyl)androst-4-en-3-one 6-Ethoxybenzothiazole-2-thiol (22\6) | amorphous | 70 | 5.75s(1H, H-4); 3.34t (J=7Hz, 2H, CH$_2$S); 1.21s (3H, H-19); 1.00s (3H, H-18) 7.74d(J= 9Hz, 1H, aryl); 7.22d (J=2Hz, 1H, aryl); 7.01 dd(J=9Hz+ 2Hz, 1H, aryl); 5.73s (1H, H-4); 4.07q(J= 7Hz, 2H, OEt); 3.30t (J=7Hz, 2H, CH$_2$S); 1.44t (J=7Hz, 3H, OEt); 1.21s (3H, H-19); 1.00s(3H, H-18) |
| 31 | 17β-Hydroxy-17α-(1,1,2,2,2-pentafluoroethyl)-7α-[13-[(thiazol-2-yl)sulfanyl]tridecyl]androst-4-en-3-one Thiazole-2-thiol (22\6) | Oil | 85 | 7.66d(J= 3Hz, 1H, thiazolyl); 7.20d(J= 3Hz, 1H, thiazolyl); 5.73s(1H, H-4); 3.20t (J=7Hz, 2H, CH$_2$S); 1.21s (3H, H-19); 1.00s(3H, H-18) |
| 32 | 17β-Hydroxy-7α-[13-[(4-methyl-phenyl)sulfonyl]tridecyl]-17α-(1,1,2,2,2-pentafluoroethyl)androst-4-en-3-one Sodium-4-methylbenzene-sulfinate (22\4) | Foam | 51 | 7.78dbr(J= 8Hz, 2H, aryl); 7.37 dbr(J=8Hz, 2H, aryl); 5.73s(1H, H-4); 3.06m (2H, CH$_2$SO$_2$); 2.46s(3H, tolyl); 1.21 s(3H, H-19); 1.00s(3H, H-18) |
| 33a | 3,3-[1,2-Ethanediylbis(thio)]-7α-(hex-5-enyl)-17α-(1,1,2,2,2-pentafluoroethyl)androst-4-en-17β-ol Prop-2-enylmagesium bromide (1h\1i) | Foam | 81 | 5.82ddt(J= 17Hz+10Hz+ 7Hz, 1H, vinyl); 5.46 s(1H, H-4); 5.02dbr(J= 17Hz, 1H, vinyl); 4.94 dbr(J= 10Hz, 1H, vinyl); 3.45–3.29 m(3H, dithiolane); 3.29–3.16m (1H, dithiolane); 2.39m(1H, H-12); 1.05s (3H, H-19); 0.96s(3H, H-18) |
| 33b | 3,3-[1,2-Ethanediylbis(thio)]-7α-(3-hydroxyhexyl)-17α-(1,1,2,2,2-pentafluoroethyl)androst-4-en-17β-ol Borane-dimethyl sulfide complex (33a\1f) | Foam | 69 | 5.45s(1H, H-4); 3.64 tbr(J=6Hz, 2H, CH$_2$OH); 3.44–3.29m (3H, dithiolane); 3.29–3.16m (1H, dithiolane); 2.39m(1H, H-12); 1.04s (3H, H-19); 0.96s(3H, H-18) |
| 33c | 6-[17β-Hydroxy-3-oxo-17α-(1,1,2,2,2-pentafluoroethyl)androst-4-en-7α-yl]hexyl-acetate Glyoxylic acid/Glacial acetic acid (33b\1j) | amorphous | 66 | 5.73s(1H, H-4); 4.05t (J=7Hz, 2H, CH$_2$O); 2.05s (3H, acetate); 1.21s(3H, H-19); 1.00s (3H, H-18) |
| 34 | 17β-Hydroxy-7α-(6-hydroxyhexyl)-17α-(1,1,2,2,2-pentafluoroethyl)androst-4-en-3-one Potassium carbonate/methanol (33c\1c) | Foam | 62 | 5.74s(1H, H-4); 3.64t (J=7Hz, 2H, CH$_2$O); 1.21s (3H, H-19); 1.00s(3H, H-18) |
| 35 | 6-[17β-Hydroxy-3-oxo-17α-(1,1,2,2,2-pentafluoroethyl)androst-4-en-7α-yl]hexyl-(4-methylbenzene-sulfonate) 4-Methylbenzene-sulfonyl chloride (34\1g) | Foam | 87 | 7.79d(J= 8Hz, 2H, aryl); 7.35d (J=8Hz, 2H, aryl); 5.71s (1H, H-4); 4.01t(J= 7Hz, 2H, CH$_2$OTs); 2.46 s(3H, tolyl); 1.21 s(3H, H-19); 1.00s(3H, H-18) |
| 36 | 17β-Hydroxy-7α-(6-iodohexyl)-17α-(1,1,2,2,2-pentafluoroethyl)androst-4-en-3-one Sodium iodide (35\2) | Foam | 92 | 5.73s(1H, H-4); 3.19t (J=7Hz, 2H, CH$_2$I); 1.21s (3H, H-19); 1.00s(3H, H-18) |
| 37 | 17β-Hydroxy-17α-(1,1,2,2,2-pentafluoroethyl)-7α-[6-(phenyl-sulfanyl)hexyl]androst-4-en-3-one Sodium phenyl thiolate (36\4) | Oil | 14 | 7.31dbr(J= 8Hz, 2H, aryl); 7.27 ddbr(J=8Hz+ 8Hz, 2H, aryl); 7.16 ddbr(J=8Hz+ 8Hz, 1H, aryl); 5.72s (1H, H-4) 2.91t(J= 7Hz, 2H, CH$_2$S); 1.20s (3H, H-19) 1.00s(3H, H-18) |
| 38 | 17β-Hydroxy-17α-(1,1,2,2,2-pentafluoroethyl)-7α-[6-(phenyl-sulfonyl)hexyl]androst-4-en-3-one Sodium benzene sulfinate (36\4) | Oil | 78 | 7.91dbr(J= 8Hz, 2H, aryl); 7.67 ddbr(J=8Hz+ 8Hz, 1H, aryl); 7.58 ddbr(J=8Hz+ 8Hz, 2H, aryl);. 5.69 s(1H, H-4); |

-continued

| Ex. | Product Reagent (Precursor/Process) | Form | Yield [%] | $^1$H-NMR δ |
|---|---|---|---|---|
| | | | | 3.08m(2H, CH$_2$SO$_2$); 1.20 s(3H, H-19); 1.00s(3H, H-18) |
| 39 | 17β-Hydroxy-17α-(1,1,2,2,2-pentafluoroethyl)-7α-[6-[(pyridin-2-yl)sulfanyl]hexyl]androst-4-en-3-one Pyridine-2-thiol (36\6) | Oil | 58 | 8.42dbr(J=5Hz, 1H, pyridinyl); 7.47ddd(J=8Hz+8Hz+2Hz, 1H, pyridinyl); 7.18dbr(J=8Hz, 1H, pyridinyl); 6.97ddbr(J=8Hz+5Hz, 1H, pyridinyl); 5.72s(1H, H-4); 3.05t (J=7Hz, 2H, CH$_2$S); 1.20s (3H, H-19) 1.00s(3H, H-18) |
| 40 | 17β-Hydroxy-17α-(1,1,2,2,2-pentafluoroethyl)-7α-[6-[(pyrimidin-2-yl)sulfanyl]hexyl]androst-4-en-3-one Pyrimidine-2-thiol (36\6) | Oil | 82 | 8.50d(J=5Hz, 2H, pyrimidinyl); 6.94t(J=5Hz, 1H, pyrimidinyl); 5.72s(1H, H-4); 3.12t (J=7Hz, 2H, CH$_2$S); 1.20s (3H, H-19); 1.00s(3H, H-18) |
| 41 | 7α-[6-[(4,6-Dimethylpyrimidin-2-yl)sulfanyl]hexyl]-17β-hydroxy-17α-(1,1,2,2,2-pentafluoroethyl)androst-4-en-3-one 4,6-Dimethylpyrimidine-2-thiol (36\6) | Oil | 56 | 6.67s(1H, pyrimidinyl); 5.73s(1H, H-4); 3.25t (J=7Hz, 2H, CH$_2$S); 2.40s (6H, Me); 1.20s(3H, H-19); 1.00s (3H, H-18) |
| 42 | 17β-Hydroxy-7α-[6-[(1-methyl-1H-imidazol-2-yl)sulfanyl]hexyl]-17α-(1,1,2,2,2-pentafluoroethyl)androst-4-en-3-one 1-Methyl-1H-imidazole-2-thiol (36\6) | Oil | 20 | 7.05d(J=1Hz, 1H, imidazolyl); 6.92d(J=1Hz, 1H, imidazolyl); 5.71s(1H, H-4); 3.62s (3H, Me); 3.04t(J=7Hz, 2H, CH$_2$S); 1.20s (3H, (H-19); 1.00s(3H); H-18) |
| 43 | 17β-Hydroxy-17α-(1,1,2,2,2-pentafluoroethyl)-7α-[6-[(thiazol-2-yl)sulfanyl]hexyl]androst-4-en-3-one Thiazole-2-thiol (36\6) | Oil | 68 | 7.65d(J=4 Hz, 1H, thiazolyl); 7.21d(J=4Hz, 1H, thiazolyl); 5.72s(1H, H-4); 3.20t (J=7Hz, 2H, CH$_2$S); 1.20s (3H, H-19); 1.00s(3H, H-18) |

EXAMPLE 44

7α-[9-[[(1,1-Dimethylethyl)dimethylsilyl]oxy]nonyl]-17α-methyl-3-oxoandrost-4-en-17β-yl-acetate 2.82 g of magnesium chips (116 mmol) is suspended in 56 ml of dry tetrahydrofuran, and the formation of the Grignard compound is begun with a little [(9-bromononyl)oxy](1,1-dimethylethyl)dimethylsilane, some dibromomethane and some granules of iodine. After the start-up, the solution of a total of 39.0 g of [(9-bromononyl)oxy](1,1-dimethylethyl) dimethylsilane (116 mmol) in 36 ml of dry tetrahydrofuran is added drop by drop so that the internal temperature does not exceed 35° C. Then, the solution is heated for 15 minutes to 80° C. and then mixed at −60° C. with a solution that was prepared from 11.0 g of copper(I) iodide (58 mmol) in 54 ml of dry tetrahydrofuran by adding 20.1 g of lithium bromide (132 mmol) while being cooled with ice and diluted with 21 ml of 1,3-dimethyl-3,4,5,6-tetrahydro-2(1H)-pyrimidinone. With the addition, the internal temperature is not a to exceed −50° C. After 15 minutes of stirring at −20° C., it is cooled to −70° C., and the solution of 17α-methyl-3-oxoandrosta-4,6-dien-17β-yl acetate (40 mmol), whose production is described in V. Schwarz, Collect. Czech. Chem. Commun. 26, 1958–1966 (1961), and 13 ml of chlorotrimethylsilane in 60 ml of dry tetrahydrofuran and 16 ml of 1,3-dimethyl-3,4,5,6-tetrahydro-2(1H)-pyrimidinone are quickly added so that the internal temperature does not exceed −65° C. The mixture is stirred for one hour, whereby the temperature reaches −50° C., and finally it is mixed with 16 ml of glacial acetic acid and left for another hour at room temperature. Then, the batch is diluted with ethyl acetate, shaken out with semisaturated aqueous ammonium chloride solution, with 2 molar aqueous ammonia solution and twice with saturated aqueous common salt solution, the organic phase is dried with sodium sulfate and concentrated by evaporation. The residue is chromatographed on silica gel with dichloromethane/hexane, and the yield is 13.9 g. (57% of theory) of the title compound. Then, 4 g of 7β-[9-[[(1,1-dimethylethyl)dimethylsilyl]oxy]nonyl]-17α-methyl-3-oxoandrost-4-en-17β-yl acetate (15% of theory) is isolated. Both compounds are oily and were characterized by MS: Cld. 600, Fnd. 600.

The following compounds were obtained analogously:

| Ex. | Product Reagent (Precursor/Process) | Form | Yield [%] | MS Cld. | MS Fnd. |
|---|---|---|---|---|---|
| 45 | 7α-[7-[[(1,1-Dimethylethyl)dimethyl-silyl]oxy]heptyl]-17α-methyl-3-oxoandrost-4-en-17β-yl-acetate [(7-Bromoheptyl)oxy](1,1-dimethylethyl)dimethylsilane | Oil | 51 | 572 | 572 |

| Ex. | Product Reagent (Precursor/Process) | Form | Yield [%] | MS Cld. | MS Fnd. |
|---|---|---|---|---|---|
| 46 | (17α-Methyl-3-oxoandrosta-4,6-dien-17β-yl-acetate\44) 7α-[10-[[(1,1-Dimethylethyl)dimethyl-silyl]oxy]decyl]-17α-methyl-3-oxoandrost-4-en-17β-yl-acetate [(10-Bromodecyl)oxy](1,1-dimethylethyl)dimethylsilane (17α-Methyl-3-oxoandrosta-4,6-dien-17β-yl-acetate\44) | Oil | 56 | 615 | 615 |
| 47 | 7α-[11-[[(1,1-Dimethylethyl)dimethyl-silyl]oxy]undecyl]-17α-methyl-3-oxoandrost-4-en-17β-yl acetate [(11-Bromoundecyl)oxy](1,1-dimethylethyl)dimethylsilane (17α-Methyl-3-oxoandrosta-4,6-dien-17β-yl-acetate\44) | Oil | 60 | 629 | 629 |
| 48 | 7α-[7-(4-Chlorobutoxy)heptyl]-17α-methyl-3-oxoandrost-4-en-17β-yl-acetate 1-Bromo-7-(4-chlorobutoxy)heptane (17α-Methyl-3-oxoandrosta-4,6-dien-17β-yl-acetate\44) | Oil | 51 | 548 550 | 548 550 |

EXAMPLE 49

7α-(9-Hydroxynonyl)-17α-methyl-3-oxoandrost-4-en-17β-yl-acetate 13.9 g of the compound (23 mmol) that is produced under 44) is dissolved in 150 ml of methanol/tetrahydrofuran (2:1), 25 ml of 8% aqueous sulfuric acid is added, and it is stirred for 2 hours at room temperature. Then, it is diluted with ethyl acetate, washed out with saturated aqueous common salt solution, and the organic phase is concentrated by evaporation with sodium sulfate after drying. The residue is chromatographed on silica gel with dichloromethane/hexane, and the yield is 10.8 g (96% of theory) of the title compound.

EXAMPLE 50

7α-(9-Chlorononyl)-17α-methyl-3-oxoandrost-4-en-17β-yl-acetate 10.8 g of the compound that is produced under 49) is dissolved in 100 ml of tetrachloromethane and 35 ml of acetonitrile and reacted with 10.5 g of triphenylphosphine (40 mmol) at room temperature for 1 hour. Then, it is diluted with dichloromethane, shaken out with saturated aqueous sodium bicarbonate and common salt solution, and the organic phase is dried wtih sodium sulfate and concentrated by evaporation. The oily residue is chromatographed on silica gel with hexane/ᵗbutyl methyl ether, yield 10.2 g (91% of theory) of the title compound.

The following compounds were obtained analogously:

| Ex. | Product Reagent (Precursor/Process) | Form | Yield [%] | MS Cld. | MS Fnd. |
|---|---|---|---|---|---|
| 51 | 7α-(9-Chlorononyl)-17β-hydroxy-17α-methyl-androst-4-en-3-one Potassium carbonate/methanol (50\1c) | Oil | 54 | 462 464 | 462 464 |
| 52 | 17β-Hydroxy-7α-(9-iodononyl)-17α-methylandrost-4-en-3-one Sodium iodide (51\2) | Oil | 80 | 554 | 554 |
| 53 | 17β-Hydroxy-7α-(9-hydroxynonyl)-17α-methylandrost-4-en-3-one Potassium carbonate/methanol (49\1c) | Foam | 74 | 444 | 444 |
| 54 | 7α-(7-Hydroxyheptyl)-17α-methyl-3-oxoandrost-4-en-17β-yl-acetate Sulfuric acid (45\49) | Oil | 98 | 456 | 458 |
| 55 | 17β-Hydroxy-7α-(7-hydroxyheptyl)-17α-methylandrost-4-en-3-one Potassium carbonate/methanol (54\1c) | Foam | 53 | 416 | 416 |
| 56 | 7α-(7-Chloroheptyl)-17β-hydroxy-17α-methyl-androst-4-en-3-one Tetrachloromethane/triphenylphosphine (55\50) | Oil | 80 | 434 436 | 434 436 |
| 57 | 17β-Hydroxy-7α-(7-iodoheptyl)-17α-methylandrost-4-en-3-one Sodium iodide (56\2) | Flash Point 116° C. | 87 | 526 | 526 |
| 58 | 7α-(7-Bromoheptyl)-17β-hydroxy-17α-methyl-androst-4-en-3-one Tetrabromomethane/triphenylphosphine (55\50) | Oil | 55 | 479 481 | 479 481 |
| 59 | 7α-(10-Hydroxydecyl)-17α-methyl-3-oxoandrost-4-en-17β-yl-acetate Sulfuric acid (46\49) | Oil | 95 | 500 | 500 |
| 60 | 17β-Hydroxy-7α-(10-hydroxydecyl)-17α-methylandrost-4-en-3-one Potassium carbonate/methanol (59\1c) | Oil | 96 | 458 | 458 |
| 61 | 7α-(10-Chlorodecyl)-17β-hydroxy-17α-methyl-androst-4-en-3-one Tetrachloromethane/triphenylphosphine (60\50) | Oil | 24 | 476 478 | 476 478 |
| 62 | 7α-(11-Hydroxyundecyl)-17α-methyl-3-oxoandrost-4-en-17β-yl-acetate Sulfuric acid (47\49) | Oil | 95 | 514 | 514 |
| 63 | 17β-Hydroxy-7α-(11-hydroxyundecyl)-17α-methylandrost-4-en-3-one Potassium carbonate/methanol (62\1c) | Oil | 49 | 472 | 472 |

-continued

| Ex. | Product Reagent (Precursor/Process) | Form | Yield [%] | MS Cld. | MS Fnd. |
|---|---|---|---|---|---|
| 64 | 7α-(11-Bromoundecyl)-17β-hydroxy-17α-methylandrost-4-en-3-one Tetrabromomethane/triphenylphosphine (63\50) | Oil | 86 | 535 537 | 535 537 |
| 65 | 7α-[7-(4-Chlorobutoxy)heptyl]-17β-hydroxy-17α-methylandrost-4-en-3-one Potassium carbonate/methanol (48\1c) | Oil | 78 | 506 508 | 506 508 |
| 66 | 17β-Hydroxy-7α-[7-(4-iodobutoxy)heptyl]-17α-methylandrost-4-en-3-one Sodium iodide (65\2) | Oil | 92 | 598 | 598 |
| 67 | 17β-Hydroxy-17α-methyl-7α-[7-(phenylsulfanyl)heptyl]androst-4-en-3-one Sodium phenyl thiolate (57\4) | Oil | 74 | 508 | 508 |
| 68 | 17β-Hydroxy-17α-methyl-3-oxoandrost-4-ene-7α-decane nitrile Potassium cyanide (52\3) | Oil | 44 | 453 | 453 |

EXAMPLE 69

17β-Hydroxy-17α-methyl-7α-[9-[(4,4,5,5,5-pentafluoropentyl)sulfanyl]nonyl]androst-4-en-3-one 0.07 ml of a 30% solution of sodium methanolate in methanol (0.33 mmol) is added to a solution of 69 mg of thioacetic acid-S-(4,4,5,5,5-pentafluoropentyl)ester (0.3 mmol), whose production is described in Li et al., Tetrahedron Lett. 35, 9141–9144 (1994), in 0.7 ml of methanol, and it is stirred for 30 minutes at room temperature. Then, a solution of 128 mg of the compound (0.23 mmol), produced under 52), in 2.3 ml of N,N-dimethylformamide is added. The reaction mixture is stirred overnight at room temperature, mixed with water and extracted three times with ethyl acetate. The organic phase is washed in succession with water and saturated aqueous sodium chloride solution, dried on sodium sulfate, filtered and concentrated by evaporation in a vacuum. The residue is chromatographed on silica gel with ethyl acetate/hexane, and the yield is 95 mg (66% of theory) of the title compound. MS: Cld. 620, Fnd. 620.

The following compounds were obtained analogously:.

| Ex. | Product Reagent (Precursor/Process) | Form | Yield [%] | MS Cld. | MS Fnd. |
|---|---|---|---|---|---|
| 70 | 7α-[9-(Acetylsulfanyl)nonyl]-17β-hydroxy-17α-methylandrost-4-en-3-one Potassium thioacetate (52\3) | Oil | 99 | 502 | 502 |
| 71 | 17β-Hydroxy-17α-methyl-7α-[9-(pentylsulfanyl)nonyl]androst-4-en-3-one 1-Iodopentane (70\69) | Oil | 32 | 530 | 530 |
| 72 | 17β-Hydroxy-17α-methyl-7α-[9-(phenylsulfanyl)nonyl]androst-4-en-3-one Sodium phenyl thiolate (52\4) | Oil | 62 | 536 | 536 |
| 73 | 5-[[9-(17β-Hydroxy-17α-methyl-3-oxoandrost-4-en-7α-yl)nonyl]sulfanyl]pentanoic acid-methyl-ester 5-Iodopentanoic acid-methyl ester (70\69) | Oil | 39 | 574 | 574 |
| 74 | 7α-[9-[(5-Chloropentyl)-sulfanyl]nonyl]-17β-hydroxy-17α-methylandrost-4-en-3-one 1-Chloro-5-iodopentane (70\69) | Oil | 42 | 564 566 | 564 566 |
| 75 | 5-[[9-(17β-Hydroxy-17α-methyl-3-oxoandrost-4-en-7α-yl)nonyl]sulfanyl]pentanenitrile 5-Bromopentanenitrile (70\69) | Oil | 36 | 541 | 541 |
| 76a | 7α-[9-[[5-[[(1,1-Dimethylethyl)dimethyl-silyl]oxy]pentyl]sulfanyl]nonyl]-17β-hydroxy-17α-methylandrost-4-en-3-one [(5-Bromopentyl)oxy](1,1-dimethylethyl)dimethylsilane (70\69) | Oil | 98 | 661 | 661 |
| 76b | 17β-Hydroxy-7α-[9-[(5-hydroxypentyl)sulfanyl]nonyl]-17α-methylandrost-4-en-3-one Sulfuric acid (76a\49) | Oil | 32 | 546 | 546 |
| 77 | 7α-[9-[(5-Bromopentyl)-sulfanyl]nonyl]-17β-hydroxy-17α-methylandrost-4-en-3-one Tetrabromomethane/triphenylphosphine (76b\50) | Oil | 26 | 609 611 | 609 611 |
| 78 | 7α-(9-Azidononyl)-17β-hydroxy-17α-methyl-androst-4-en-3-one Sodium azide (52\3) | Oil | 66 | 469 | 469 |
| 79 | 7α-[9-(Butylmethyl-amino)nonyl]-17β-hydroxy-17α-methylandrost-4-en-3-one Butylmethylazan/bis(1-methylethyl)ethylazan (52\3) | Oil | 35 | 513 | 513 |
| 80 | 7α-[7-(Acetylsulfanyl)heptyl]-17β-hydroxy-17α-methylandrost-4-en-3-one Potassium thioacetate (57\3) | Oil | 80 | 474 | 474 |
| 81 | 17β-Hydroxy-17α-methyl-7α-[7-[(4,4,5,5,5-pentafluoropentyl)sulfanyl]-heptyl]androst-4-en-3-one Thioacetic acid-S-(4,4,5,5,5-pentafluoropentyl)ester (57\69) | Oil | 84 | 592 | 592 |
| 82 | 7α-(7-(Butylmethyl-amino)heptyl]-17β-hydroxy-17α-methylandrost-4-en-3-one Butylmethylazan/bis(1-methylethyl)ethylazan (57\3) | Oil | 32 | 485 | 485 |
| 83 | N-[7-(17β-Hydroxy-17α-methyl-3-oxoandrost-4-en-7α-yl)heptyl]pentanamide | Oil | 18 | 499 | 499 |

-continued

| Ex. | Product Reagent (Precursor/Process) | Form | Yield [%] | MS Cld. | MS Fnd. |
|---|---|---|---|---|---|
| | Pentanamide (57\6) | | | | |
| 84 | 17β-Hydroxy-17α-methyl-3-oxoandrost-4-en-7α-octanenitrile Potassium cyanide (57\3) | Oil | 56 | 425 | 425 |
| 85 | 7α-(7-Azidoheptyl)-17β-hydroxy-17α-methyl-androst-4-en-3-one Sodium azide (57\3) | Oil | 77 | 441 | 441 |
| 86 | N-[7-(17β-Hydroxy-17α-methyl-3-oxoandrost-4-en-7α-yl)heptyl]methanesulfonamide Methanesulfonamide (57\6) | Oil | 63 | 493 | 493 |
| 87 | 5-[[7-(17β-Hydroxy-17α-methyl-3-oxoandrost-4-en-7α-yl)heptyl]oxy]pentanenitrile Potassium cyanide (66\3) | Oil | 80 | 497 | 497 |
| 88 | 17β-Hydroxy-7α-[7-(4-methoxybutoxy)heptyl]-17α-methylandrost-4-en-3-one Sodium methanolate/methanol (66\4) | Oil | 48 | 502 | 502 |
| 89 | 7α-[7-[(But-3-enyl)oxy]heptyl]-17β-hydroxy-17α-methylandrost-4-en-3-one Sodium methanolate/methanol (66\4) | Oil | 14 | 470 | 470 |
| 90 | 17β-Hydroxy-17α-methyl-7α-[11-[(4,4,5,5,5-pentafluoropentyl)sulfanyl]undecyl]androst-4-en-3-one Thioacetic acid-S-(4,4,5,5,5-pentafluoropentyl)ester (64\69) | Oil | 62 | 648 | 648 |
| 91 | 17β-Hydroxy-17α-methyl-7α-[11-(phenylsulfanyl)undecyl]androst-4-en-3-one Sodium phenyl thiolate (64\4) | Oil | 75 | 564 | 564 |
| 92 | 17β-Hydroxy-7α-(11-methoxyundecyl)-17α-methylandrost-4-en-3-one Sodium methanolate/methanol (64/4) | Oil | 57 | 486 | 486 |

EXAMPLE 93

17β-Hydroxy-17α-methyl-7α-[9-[(4,4,5,5,5-pentafluoroientyl)sulfinyl]nonyl]androst-4-en-3-one 83 mg of the compound that is produced under 69) is dissolved in 5 ml of dichloromethane, cooled in an ice bath, and 32 mg of 70% 3-chloroperbenzoic acid is added. After 15 minutes of stirring, it is mixed with saturated aqueous sodium thiosulfate solution, stirred for another 15 minutes and then diluted with dichloromethane. The organic phase is washed with saturated aqueous sodium bicarbonate solution and common salt solution, dried with sodium sulfate and concentrated by evaporation. The residue is chromatographed on silica gel on a thin-layer plate with acetone/hexane, and the yield is 52 mg (62% of theory) of the title compound. MS: Cld. 636, Fnd. 636.

The following compounds were obtained analogously:

| Ex. | Product Reagent (Precursor\Process) | Form | Yield [%] | MS Cld. | MS Fnd. |
|---|---|---|---|---|---|
| 94 | 17β-Hydroxy-17α-methyl-7α-[7-[(4,4,5,5,5-pentafluoropentyl)sulfinyl]heptyl]androst-4-en-3-one 3-Chloroperbenzoic acid (81\93) | Oil | 65 | 608 | 608 |
| 95 | 17β-Hydroxy-17α-methyl-7α-[7-[(4,4,5,5,5-pentafluoropentyl)sulfonyl]heptyl]androst-4-en-3-one 3-Chloroperbenzoic acid (81\93) | Oil | 7 | 624 | 624 |
| 96 | 17β-Hydroxy-17α-methyl-7α-[11-[(4,4,5,5,5-pentafluoropentyl)sulfinyl]undecyl]androst-4-en-3-one 3-Chloroperbenzoic acid (90\93) | Oil | 66 | 664 | 664 |
| 97 | 17β-Hydroxy-17α-methyl-7α-[11-[(4,4,5,5,5-pentafluoropentyl)sulfonyl]undecyl]androst-4-en-3-one 3-Chloroperbenzoic acid (90\93) | Oil | 12 | 680 | 680 |
| 96 | 17β-Hydroxy-17α-methyl-7α-[7-(phenylsulfinyl)heptyl]androst-4-en-3-one 3-Chloroperbenzoic acid (67\93) | Oil | 57 | 524 | 524 |
| 99 | 17β-Hydroxy-17α-methyl-7α-[7-(phenylsulfonyl)heptyl]androst-4-en-3-one 3-Chloroperbenzoic acid (67\93) | Oil | 26 | 540 | 540 |
| 100 | 17β-Hydroxy-17α-methyl-7α-(9-sulfanylnonyl)androst-4-en-3-one Potassium carbonate/methanol (70\1c) | Oil | 43 | 460 | 460 |

EXAMPLE 101

17β-Hydroxy-17α-methyl-3-oxoandrost-4-ene-7α-heptanoic Acid 416 mg of the compound (1 mmol) that is produced under 55) is dissolved in 10 ml of anhydrous acetone and mixed with 5 ml of a 1 molar solution of Jones reagent (chromate solution) while being cooled with ice. After 15 minutes, it is mixed with saturated aqueous sodium sulfite solution, the acid solution is shaken out with ethyl acetate, the organic phase is extracted with saturated aqueous common salt solution, dried with sodium sulfate and concentrated by evaporation. The residue is chromatographed on silica gel with acetone/hexane, and the yield is 78 mg (18% of theory) of the title compound. MS: Cld. 430, Fnd. 430.

EXAMPLE 102

N-Butyl-17β-hydroxy-N,17α-dimethyl-3-oxoandrost-4-ene-7α-heptanamide 78 mg of the compound that is produced under 101) is dissolved in 6 ml of dichloromethane, cooled to −10° C. and mixed in succession with 30 µl of 4-methylmorpholine, 30 µl of chloroformic acid-(2-methylpropyl)ester and after 10 minutes with 40 µl of butylmethylazan. After 1 hour of stirring at room temperature, it is diluted with dichloromethane, extracted in succession with 1 molar aqueous sulfuric acid, saturated aqueous sodium bicarbonate solution and saturated common salt solution, the organic phase is dried with sodium sulfate and concentrated by evaporation. The residue is chromatographed on silica gel with acetone/hexane, and the yield is 40 mg (45% of theory) of the title compound. MS: Cld. 499, Fnd. 499.

The following compounds were obtained analogously:

| Ex. | Product Reagent (Precursor\Process) | Form | Yield [%] | MS Cld. | MS Fnd. |
|---|---|---|---|---|---|
| 103 | 17β-(Acetyloxy)-17α-methyl-3-oxoandrost-4-ene-7α-nonanoic acid<br>Jones reagent<br>(49\101) | Oil | 13 | 500 | 500 |
| 104 | 17β-(Acetyloxy)-N-butyl-N,17α-dimethyl-3-oxoandrost-4-ene-7α-nonanamide<br>4-Methylmorpholine/chloroformic acid-(2-methylpropyl)ester/butyl-methylazan<br>(103\102) | Oil | 90 | 569 | 569 |
| 105 | N-Butyl-17β-hydroxy-N,17α-dimethyl-3-oxo-androst-4-ene-7α-nonanamide<br>Potassium carbonate/methanol<br>(104\1c) | Oil | 22 | 527 | 527 |
| 106 | 17β-(Acetyloxy)-17α-methyl-3-oxoandrost-4-ene-7α-undecanoic acid<br>Jones reagent<br>(62\101) | Oil | 15 | 528 | 528 |
| 107 | 17β-(Acetyloxy)-N-butyl-N,17α-dimethyl-3-oxoandrost-4-ene-7α-undecanamide<br>4-methylmorpholine/chloroformic acid-(2-methylpropyl)ester/butyl-methylazan<br>(106\102) | Oil | 86 | 597 | 597 |
| 108 | N-Butyl-17β-hydroxy-N,17α-dimethyl-3-oxo-androst-4-ene-7α-undecanamide<br>Potassium carbonate/methanol<br>(107\1c) | Oil | 35 | 555 | 555 |

EXAMPLE 109

2-[9-(17β-Hydroxy-17α-methyl-3-oxoandrost-4-en-7α-yl)nonyl]propanedioic Acid-diethyl Ester 109a) 7α-(9-Chlorononyl)-3,3-[1,2-ethanediylbis(oxy)]-17α-methylandrost-4-en-17β-ol 1.48 g of the compound that is produced under 51) is dissolved in 20 ml of dichloromethane, and 20 ml of 1,2-ethanediol, 12 ml of trimethoxymethane and 0.6 g of pyridinium-p-toluenesulfonate are added. The mixture is stirred overnight at room temperature, then mixed wtih triethylazan, diluted with dichloromethane and shaken out with water and saturated aqueous common salt solution. The organic phase is dried with sodium sulfate, concentrated by evaporation and chromatographed on silica gel with hexane/ᵗbutyl methyl ether. The yield is 1.12 g (69% of theory) of the title compound. MS: Cld. 506/508; Fnd. 506/508.

109b) 3,3-[1,2-Ethanediylbis(oxy)]-7α-(9-iodononyl)-17α-methylandrost-4-en-17β-ol 1.09 g of the compound that is produced under 109a) is reacted analogously to the process that is described in Example 2) with 1.5 g of sodium iodide to form 1.37 g of the title compound as a colorless oil. MS: Cld. 598, Fnd. 598

109c) 2-[9-(17β-Hydroxy-17α-methyl-3-oxoandrost-4-en-7α-yl)nonyl]propanedioic Acid-diethyl Ester 80 mg of propanedioic acid-diethyl ester in 0.5 ml of anhydrous tetrahydrofuran is deprotonated with 12 mg of 80% sodium hydride, 60 mg of the compound (0.1 mmol), produced under 109b), in 1 ml of anhydrous N,N-dimethylformamide is added, and it is heated for 5 hours to 80° C. After cooling, it is worked up as usual with ethyl acetate. The residue is dissolved in 0.5 ml of acetone and stirred with 0.1 ml) of 4 molar aqueous hydrochloric acid for 15 minutes at room temperature. Then, it is worked up with ethyl acetate again and chromatographed. The yield is 29 mg (49% of theory) of the title compound. MS: Cld. 586, Fnd. 586.

The following compounds were obtained analogously:

| Ex. | Product Reagent (Precursor\Process) | Form | Yield [%] | MS Cld. | MS Fnd. |
|---|---|---|---|---|---|
| 110 | 2-[2-Acetyl-9-(17β-hydroxy-17α-methyl-3-oxoandrost-4-en-7α-yl)nonyl]undecanoic acid ethyl ester<br>3-Oxobutanoic acid ethyl ester<br>(109b\109c) | Oil | 51 | 556 | 556 |
| 111 | 17β-Hydroxy-17α-methyl-7α-[9-(pentyloxy)nonyl]androst-4-en-3-one<br>1-Pentanol<br>(109b\109c) | Oil | 23 | 514 | 514 |
| 112 | N-[9-(17β-Hydroxy-17α-methyl-3-oxoandrost-4-en-7α-yl)nonyl]pentanamide<br>Pentanamide<br>(109b\109c) | Oil | 21 | 527 | 527 |
| 113 | N-[9-(17β-Hydroxy-17α-methyl-3-oxoandrost-4-en-7α-yl)nonyl]methanesulfonamide<br>Methanesulfonamide<br>(109b\109c) | Oil | 57 | 521 | 521 |

EXAMPLE 114

7α-(9-Chlorononyl)-6β-hydroxy-17α-methyl-3-oxoandrost-4-en-17β-yl-acetate 3.3 g of the compound that is produced under 50) is dissolved in 22 ml of 2,2-dimethoxypropane, 0.4 g of pyridinium-p-toluenesulfonate is added, and it is refluxed for 22 hours. After the cooling, it is mixed with triethylazan and evaporated to the dry state. The residue is chromatographed on silica gel with hexane/ᵗbutyl methyl ether. 2.91 g of 7α-(9-chlorononyl)-3-methoxy-17α-methylandrosta-3,5-dien-17β-yl-acetate-(84% of theory) is obtained and is immediately further reacted.

This substance is suspended in 60 ml of a mixture of ethanol/water 95:5, mixed with 1.7 g of 3-chloroperbenzoic acid (6.8 mmol) and stirred for 45 minutes at room temperature. Then, 5 ml of 2 molar aqueous sulfuric acid is added, stirred for 15 a minutes at room temperature and diluted with ethyl acetate. The organic phase is shaken out with water and saturated aqueous solutions of sodium dithionate, sodium bicarbonate and common salt, dried with sodium sulfate and concentrated by evaporation. After chromatography on silica gel with hexane/ethyl acetate, 1.0 g (30% of theory) of the title compound is obtained. MS: Cld. 520/522, Fnd. 520/522.

The following compounds were obtained analogously:

| Ex. | Product Reagent (Precursor\Process) | Form | Yield [%] | MS Cld. | MS Fnd. |
|---|---|---|---|---|---|
| 115 | 6β-Hydroxy-7α-(9-hydroxynonyl)-17α-methyl-3-oxoandrost-4-en-17β-yl-acetate 3-chloroperbenzoic acid (49\114) | Oil | 8 | 502 | 502 |
| 116 | 6β,17β-Dihydroxy-7α-(7-hydroxyheptyl)-17α-methylandrost-4-en-3-one 3-Chloroperbenzoic acid (55\114) | Oil | 9 | 432 | 432 |
| 117 | 6β,17β-Dihydroxy-17α-methyl-3-oxoandrost-4-en-7α-octane-nitrile 3-Chloroperbenzoic acid (84\114) | Oil | 8 | 441 | 441 |
| 118 | 7α-[7-(4-Chlorobutoxy)heptyl]-6β,17β-dihydroxy-17α-methylandrost-4-en-3-one 3-Chloroperbenzoic acid (65\114) | Oil | 14 | 522 524 | 522 524 |

EXAMPLE 119

Antiproliferation Test with the Human Prostate Cancer Cell Line (LNCaP)

The human prostate cancer cell line LNCaP [American Type Culture Collection (ATCC)=Accession No.: CRL 1740; Horoszewicz et al., Cancer Research, 43 pp. 1809–18, 1983] was isolated from the lymph node metastasis of a prostate cancer patient. It expresses the androgen receptor and can be stimulated in growth by androgens. The androgen-mediated growth stimulation can be blocked by simultaneous administration of antiandrogens. The antiandrogenic active strength (IC50) of test compounds can be determined by dose-action correlations. If a single administration of a test compound leads to growth stimulation, this can be explained by an androgenic action which the compounds according to the invention are not to exhibit.

Execution:

The cells are cultivated in RPMI 1640 medium with penicillin (10,000 units/l), streptomycin (100 mg/l), glutamine (200 mmol), 10% fetal calf serum and 0.1 nM of the synthetic androgen R1881 (Metribolone, Roussel).

Day 1: Sowing of the cells in a density of 5,000–6,000/100 μl/hole in 96-hole plates. Adding test compound (100 μl/hole doubly concentrated) to the culture medium with 0.2 nM of R1881 (yields 0.1 nM final concentration). Incubation of the cells for 72 or 96 hours at 37° C., 5% $CO_2$, 90% relative atmospheric humidity. In the culture medium, the fetal calf serum is replaced by 5% activated carbon-treated (steroid-free) serum.

Day 3 or 4: Medium change: In each case in 50% of the medium, inclusive test compounds are replaced by fresh medium. Incubation of the cells for 96 or 72 hours at 37° C., 5% CO2, 90% relative atmospheric humity.

Day 7: Adding 25 μl of MTT solution per hole {MTT= (3[4,5-dimethylthiazol-2-yl]-2,5-diphenaltetrazolium bromide (thiazolyl blue}. Incubation is for 3 hours at 37° C., 5% $CO_2$, 90% relative atmospheric humidity. After the removal of the supernatant, addition of 100 μl of DMSO per hole. Measurement of the optical density at 570 mm.

The antiandrogens OH-flutamide and casodex that are found in clinical practice were tested, as well as the compound EM-101 (N-butyl, N-methyl-11-(17'β-hydroxy-4'-androsten-3'-on-7'α-yl)undecanamide of WO 91/00732.

Results:

| | Antiandrogeneity IC50 in the presence of 0.1 nM of R1881 | Androgeneity at 1 μM* |
|---|---|---|
| OH-flutamide | >10,000 nM | 144% |
| Casodex | 440 nM | 7% |
| EM-101 | 4440 nM | 0% |
| Example 53 | 40 nM | 0% |
| Example 20 | 200 nM | 0% |
| Example 87 | 82 nM | 0% |

*The growth stimulation by 0.1 nM of R1881 was set = 100%.

The results show that the compounds according to the invention exert no androgenic action in the case of an improved antiandrogenic action (lower $IC_{50}$ values).

What is claimed is:

1. A testosterone compound of formula I

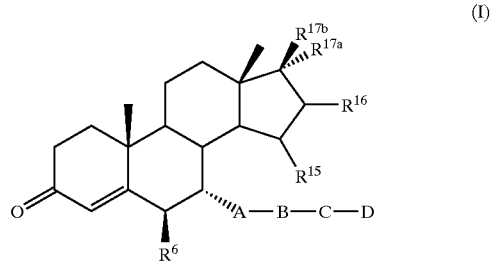

(I)

in which $R^6$ is a hydrogen atom, a hydroxy group, a $C_1$–$C_{10}$ alkoxy group, a $C_1$–$C_{10}$ alkanoyloxy group or a halogen atom, $R^{15}$ and $R^{16}$ each are a hydrogen atom or together form a bond, $R^{17a}$ is a $C_1$–$C_4$ alkyl group, a $C_2$–$C_4$ alkinyl group, or a radical of formula $C_nF_mH_o$, wherein n=1, 2, 3 or 4, m>1 and m+o=2n+1, $R^{17b}$ is a hydroxy group, a $C_1$–$C_{10}$ alkoxy group or a $C_1$–$C_{10}$ alkanoyloxy group, A is an unbranched $C_6$–$C_{13}$ alkylene group, B is an oxygen atom, a —S(O)$_p$ group, wherein p=0, 1 or 2, an iminocarbonyl group —C(O)N(Y)—, an imino group —N(Y)—, a carbonylimino group —N(Y)C(O)—, a sulfonylimino group —N(Y)S(O)$_2$—, wherein Y is a hydrogen atom or a $C_1$–$C_8$ alkyl group, a sulfonyloxy group —OS(O)$_2$—, a dimethylsilyloxy group —O—Si(CH$_3$)$_2$— or a carbonylsulfanyl group —SC(O)—, or B is a bond between A and C, or together with C forms a bond between A and D, C is a bond between B and D, or together with B forms a bond between A and D or an unbranched $C_1$–$C_6$ alkylene group, a phenylene group, a substituted phenylene group, a five-ring or six-ring heteroarylene group, a substituted five-ring or six-ring heteroarylene group, or a five-ring or six-ring heteroarylene group that is condensed with a phenyl ring, and D is a hydrogen atom, a $C_1$–$C_4$ alkyl group, a vinyl group, a $C_1$–$C_4$ alkoxy group, a $C_1$–$C_4$ alkoxycarbonyl group, a bis($C_1$–$C_4$ alkoxycarbonyl)methyl group, an acetyl ($C_1$–$C_4$ alkoxycarbonyl)methyl group, a cyano group, a carboxy group, an azide group, a hydroxy group, a halogen atom or a radical of formula $C_nF_mH_o$, wherein n=1, 2, 3 or 4, m>1 and m+o=2n+1.

2. A testosterone compound according to claim 1, wherein $R^{17a}$ is a methyl group, an ethyl group, a trifluoromethyl group or a pentafluoroethyl group.

3. A testosterone compound according to claim 1, wherein $R^{17b}$ is a hydroxy group, a $C_1$–$C_5$ alkoxy group or a $C_1$–$C_3$ alkanoyloxy group.

4. A testosterone compound according to claim 3, wherein $R^{17b}$ is a hydroxy, methoxy, ethoxy or acetyloxy group.

5. A testosterone compound according to claim 1, wherein $R^6$ is a hydrogen atom, a hydroxy group or a halogen atom.

6. A testosterone compound according to claim 1, wherein $R^{15}$ and $R^{16}$ each represent a hydrogen atom.

7. A testosterone compound according to claim 1, wherein radical ABCD is 9-hydroxynonyl, 7-(acetylsulfanyl)heptyl or 7-(4-cyanobutoxy)heptyl.

8. A testosterone compound according to claim 1, wherein the five-ring- or six-ring-heteroaromatic compound of radical C is pyrrole, thiophene, imidazole, thiazole, oxazole, triazole, thiadiazole, indole, benzoxazole, benzothiazole, pyridine, or pyrimidine.

9. A testosterone compound according to claim 1, that is
7α-(9-Chlorononyl)-17α-methyl-3-oxoandrost-4-en-17β-yl-acetate,
7α-(9-Chlorononyl)-17β-hydroxy-17α-methylandrost-4-en-3-one,
17β-Hydroxy-7α-(9-iodononyl)-17α-methylandrost-4en-3-one,
17β-Hydroxy-7α-(9-hydroxynonyl)-17α-methylandrost-4-en-3-one,
7α-(10-Chlorodecyl)-17β-hydroxy-17α-methylandrost-4-en-3-one,
17β-Hydroxy-7α-(11-hydroxyundecyl)-17α-methylandrost-4-en-3-one,
7α-(11-Bromoundecyl)-17β-hydroxy-17α-methylandrost-4-en-3-one,
17β-Hydroxy-17α-methyl-7α-[7-(phenylsulfanyl)heptyl]androst-4-en-3-one,
17-β-Hydroxy-17α-methyl-7α-[9-[(4,4,5,5,5-pentafluoropentyl)sulfanyl]nonyl]androst-4-en-3-one
17β-Hydroxy-17α-methyl-7α-[9-(phenylsulfanyl)nonyl]androst-4-en-3-one,
7α-[9-[(5-Chloropentyl)sulfanyl]nonyl]-17β-hydroxy-17α-methylandrost-4-en-3-one,
17α-Hydroxy-7α-[9-[(5-hydroxypentyl)sulfanyl]nonyl]-17α-methylandrost-4-en-3-one,
7α-(9-Azidononyl)-17β-hydroxy-17α-methylandrost-4-en-3-one,
7α-[7-(Acetylsulfanyl)heptyl]-17β-hydroxy-17α-methylandrost-4-en-3-one,
17β-Hydroxy-17α-methyl-7α-[7-[(4,4,5,5,5-pentafluoropentyl)sulfanyl]heptyl]androst-4-en-3-one,
N-[7-(17β-Hydroxy-17α-methyl-3-oxoandrost-4-en-7α-yl)heptyl]pentanamide,
17β-Hydroxy-17α-methyl-3-oxoandrost-4-en-7α-octane nitrile,
5-[[7-(17β-Hydroxy-17α-methyl-3-oxoandrost-4-en-7α-yl)heptyl]oxy]pentanenitrile,
17β-Hydroxy-17α-methyl-7α-[9-[(4,4,5,5,5-pentafluoropentyl)sulfinyl]nonyl]androst-4-en-3-one,
N-[9-(17β-Hydroxy-17α-methyl-3-oxoandrost-4-en-7α-yl)nonyl]methanesulfonamide, or
7α-(9-Chlorononyl)-6β-hydroxy-17α-methyl-3-oxoandrost-4-en-17β-yl-acetate.

10. A pharmaceutical composition comprising at least one testosterone compound of formula I according to claim 1 and one or more physiologically acceptable adjuvants and/or vehicles.

11. A method for the long-term antiandrogen therapy of an androgen-dependent disease comprising administering to a patient in need thereof a pharmaceutical composition in accord with claim 10.

12. A method according to claim 11, wherein the androgen-dependent disease is prostate cancer.

13. A method for the long-term antiandrogen therapy of prostate cancer comprising administering to a patient in need thereof a pharmaceutical composition comprising at least one testosterone compound of formula I according to claim 9 and one or more physiologically acceptable adjuvants and/or vehicles.

14. A method for the long-term antiandrogen therapy of prostate cancer comprising administering to a patient in need thereof a pharmaceutical composition comprising 17β-Hydroxy-7α-(9-hydroxynonyl)-17α-methylandrost-4-en-3-one, 7α-[7-(Acetylsulfanyl)heptyl]-17β-hydroxy-17α-methylandrost-4-en-3-one, or 5-[[7-(17β-Hydroxy-17α-methyl-3-oxoandrost-4-en-7α-yl)heptyl]oxy]pentanenitrile according to claim 9 and one or more physiologically acceptable adjuvants and/or vehicles.

* * * * *

UNITED STATES PATENT AND TRADEMARK OFFICE
CERTIFICATE OF CORRECTION

PATENT NO. : 6,767,903 B1  
DATED : July 27, 2004  
INVENTOR(S) : Arwed Cleve et al.

It is certified that error appears in the above-identified patent and that said Letters Patent is hereby corrected as shown below:

Title page,  
Item [54], Title, "NEW7$a$-," should read -- NEW 7$a$-, --.  
Item [75], Inventors, "Muhlenpeck" should read -- Muhlenbeck --.

Column 31,  
Line 29, "-4en-" should read -- -4-en- --.  
Line 42, "17-$\beta$" should read -- 17$\beta$ --.

Column 32,  
Line 1, "17$a$-Hydroxy" should read -- 17$\beta$-Hydroxy --.

Signed and Sealed this

Seventeenth Day of May, 2005

JON W. DUDAS  
*Director of the United States Patent and Trademark Office*